(12) United States Patent
Dong et al.

(10) Patent No.: US 6,686,200 B1
(45) Date of Patent: Feb. 3, 2004

(54) METHODS AND COMPOSITIONS FOR THE LARGE SCALE PRODUCTION OF RECOMBINANT ADENO-ASSOCIATED VIRUS

(75) Inventors: Jianyun Dong, Birmingham, AL (US); Raymond A. Frizzell, Birmingham, AL (US)

(73) Assignee: UAB Research Foundation, Birmingham, AL (US)

( * ) Notice: Subject to any disclaimer, the term of this patent is extended or adjusted under 35 U.S.C. 154(b) by 1,489 days.

(21) Appl. No.: 08/114,595

(22) Filed: Aug. 31, 1993

(51) Int. Cl.$^7$ .................... C12N 5/10; C12N 15/861; C12N 15/869; C12N 15/63
(52) U.S. Cl. ............. 435/457; 435/320.1; 435/235.1; 435/455; 435/456; 435/325; 435/366; 435/69.1
(58) Field of Search ................ 435/320.1, 240.2, 435/235.1, 172.3, 455, 456, 457, 325, 366, 69.1; 424/93 A, 93.2, 93.1, 93.6

(56) References Cited

U.S. PATENT DOCUMENTS

| | | | |
|---|---|---|---|
| 5,139,941 A | | 8/1992 | Muzyczka et al. |
| 5,173,414 A | | 12/1992 | Lebkowski et al. |
| 5,252,479 A | * | 10/1993 | Srivastava ............ 435/235.1 |
| 5,354,678 A | * | 10/1994 | Lebkowski et al. ...... 435/172.3 |
| 5,587,308 A | * | 12/1996 | Carter et al. ............ 435/240.2 |

FOREIGN PATENT DOCUMENTS

EP      0 488 528 A1      6/1992

OTHER PUBLICATIONS

Berkner, BioTechniques, vol. 6, No. 7, 1988, pp. 616–629.*
Bernard Roizman et al, Herpesviruses and Their Replication, Chaper 25, 1985.*
Drumm et al. (1990), Cell 62: 1227–1233.*
Haj–Ahmad et al. (1986), J. Virol. 57(1): 267–274.*
Post et al. (1981), Cell 25: 227–232.*
Ali et al., "The use of DNA viruses as vectors for gene therapy", *Gene Therapy* (1994) 1, 367–384.

Flotte et al., "Expression of the Cystic Fibrosis Transmembrane Conductance Regulator form a Novel Adeno–associated Virus Promoter", *J. Biol. Chem.*, (1993) 268(5), 3781–3790.
Lebkowski, et al., Adeno–Associated Virus: a Vector System for Efficient Introduction and Integration of DNA into a Variety of Mammalian Cell Types, *Mol. Cell. Biol.*, 8(10) :3988–96, 1988.
Muzyczka, "The Use of Adeno–Associated Virus as a General Transduction Vector for Mammalian Cells", *Current Topics in Microbiology and Immunology*, 158:97–129, 1992.
Samulski, et al., "Targeted Integration of Adeno–Associated Virus (AAV) Into Human Chromosome 19", *Embo J.*, 10 (12) :3941–50, 1991.
Samulski, et al., "Helper–Free Stocks of Recombinant Adeno–Associated Viruses: Normal Integration Does Not Require Viral Gene Expression", *J. Virol*, 63 (9) :3822–28, 1989.
Samulski, et al., "A Recombinant Plasmid from Which an Infectious Adeno–Associated Virus Genome Can Be Excised In Vitro and Its Use To Study Viral Replication", *J. Virol*, 61 (10) :3096–3101, 1987.
Walsh, et al., Regulated High Level Expression of a Human γ—globin Gene Introduced Into Erythroid Cells By An Adeno–Associated Virus Vector, *Proc. Natl. Acad. Sci. USA*, 89:7257–61, 1992.

* cited by examiner

*Primary Examiner*—David Guzo
(74) *Attorney, Agent, or Firm*—Benjamin Aaron Adler

(57) ABSTRACT

This invention provides novel methods and compositions for use in the efficient and large-scale production of recombinant adeno-associated virus (AAV). Described herein are new producer cell lines, recombinant adenovirus or herpes virus vectors and AAV constructs. Also disclosed are particularly advantageous methods of using such materials to produce recombinant AAV virions using only the efficient process of viral infection, without requiring transfection steps. The AAV produced may be used in a variety of embodiments including, for example, for transferring exogenous genes into human cell lines and for use in human gene therapy regimens.

13 Claims, 8 Drawing Sheets

A: Lambda/HindIII
B: AdΔE3
C: AdrcE1
D: SSV9/Xba I
E: AdΔE3
F: AdrcE1
G: SSV9/Kba I

METHODS AND COMPOSITIONS FOR THE LARGE SCALE PRODUCTION OF RECOMBINANT ADENO-ASSOCIATED VIRUS

The government owns rights in the present invention pursuant to grant number DK 46177 and grant number DK 38518 from the National Institutes of Health.

BACKGROUND OF THE INVENTION

1. Field of the Invention

The present invention relates generally to the fields of molecular biology and gene transfer and particularly concerns recombinant adeno-associated virus (AAV). The invention provides novel methods and compositions, including cell lines, recombinant AAV and adenovirus or herpes virus vectors, for use in the efficient and large-scale production of adeno-associated virus. The AAV production methods described herein do not require a transfection step. The resultant AAV may be used in a variety of embodiments including, for example, for transferring exogenous genes into human cell lines and for use in human gene therapy regimens.

2. Description of the Related Art

There are currently more than 4,000 known genetic disorders which lack fully effective therapies. In recent years the prospect of using gene therapy to treat such diseases has become to be viewed as a realistic goal. The ultimate form of gene therapy requires the integration of a wild-type gene able to correct the genetic disorder into the host genome, where it can co-exist and replicate with the host DNA. The expression of the gene should be regulated at a level that can best compensate for the defective gene. In the most ideal circumstances, the disease would be cured for life by one or a few treatments, with no serious side effects.

There have been several experimental approaches to gene therapy proposed to date, but each suffer from their particular drawbacks (Mulligan, 1993). Firstly, there are basic transfection methods in which DNA containing the gene of interest is introduced into cells non-biologically, for example, by permeabilizing the cell membrane physically or chemically. This approach is limited to cells that can be temporarily removed from the body and can tolerate the cytotoxicity of the treatment, i.e. lymphocytes. Furthermore, the efficiency of gene integration is very low, on the order of one integration event per 1,000 to 100,000 cells, and expression of transfected genes is often limited to days in proliferating cells or weeks in non proliferating cells.

The retroviral vector approach capitalizes on the natural ability of viruses to enter cells, bringing their own genetic material with them. Retroviruses have the advantage that they can integrate into host genome and thus transfer the gene of interest into the genome of the target cell. However, major problems are associated with using retroviral vectors for gene therapy, for example, they only integrate efficiently into replicating cells and they are difficult to concentrate and purify.

Several DNA viruses, such as adenovirus, have also been engineered to serve as vectors for gene transfer. But many DNA viruses that can accept foreign genetic material are limited in the number of nucleotides they can accommodate and in the range of cells they infect. Moreover, adenoviruses do not integrate their genetic material into the host genome and, due to the resultant transient expression, repeated exposures would be necessary. Unfortunately, the limited serotypes of adenovirus available for vector development and host immunity pose limitations on repetitive administration.

Another limitation on adenovirus vectors is the fact that recipient cells generally express at least a low level of viral proteins in addition to the therapeutic gene (Gregory et al., 1992; Rosenfeld et al., 1992), attracting immune responses and causing inflammation in the recipient organ. The co-transfer of viral genes into recipient cells also opens the possibility that the defective viral genome can be rescued by a wild-type virus infection which may propagate the genetically engineered virus and gene among the normal population. Furthermore, studies have shown that recombinant adenovirus which are meant to be replication-defective can in fact replicate slowly (Shenk et al., 1980), raising general safety concerns.

The properties of Adenoassociated Virus (AAV), a single-stranded DNA parvovirus endogenous to the human population, make it one of the most suitable gene therapy vector candidates. Firstly, AAV is not associated with any disease (Ostrove et al., amp 1981; Cukor et al., 1984), therefore it is safe for gene transfer applications. Secondly, AAV virions are resistant to physical treatments, such as sonication and heat inactivation, that are not tolerated by other viruses during purification (Samulski et al., 1989). Thirdly, like retroviruses, AAV integrates into the host cell genome upon infection (Kotin et al., 1990; Samulski et al., 1991) so that transgenes can be expressed indefinitely. Furthermore, integration of AAV into the cellular genome is independent of cell replication (Lebkowski et al., 1988). This is particularly important as AAV can thus transfer genes into quiescent cells—which make up the vast majority of cells in the human body.

However, AAV technology does have certain limitations which remain to be overcome. For example, benefits may be realized by developing strategies to accommodate larger recombinant inserts. The major problem limiting the practical use of recombinant AAV is that AAV production methods are inefficient and laborious (Lebkowski et al., 1988; Samulski et al., 1989; Muzyczka, 1992). In recombinant AAV, key viral genes (such as cap, lip and rep) are replaced by the exogenous gene of interest. Methods for producing recombinant AAV therefore rely on co-transfecting the AAV vector carrying the gene of interest, together with a helper AAV plasmid that expresses all of the essential AAV genes, into adenovirus- or herpes-infected cells which supply the helper functions necessary for AAV replication and the production of new viral particles.

The use of cells infected with helper adenovirus or herpes virus does not create a problem, it is the transfection of the essential AAV genes which is the limiting step for the production of high titre AAV virus. Transfection of DNA molecules into cells is known to be very inefficient and the transfection-based methods generally used for AAV production are, therefore, particularly inefficient as they rely on co-transfection. Even the most-recent studies in this area have only reported a 10% increase in efficiency (Page et al., 1993). Unfortunately, new procedures, such as those utilizing chimeric Epstein Barr/AAV plasmids (Lebkowsi et al., U.S. Pat. No. 5,173,414) and transduced cells with AAV vectors stably incorporated into the genome (Muzyczka et al., U.S. Pat. No. 5,139,941), still require transfection of a helper plasmid that provides AAV genes for packaging. The production of a significant quantity of AAV virions for various applications, including clinical uses, using the current methodology thus remains impractical and a new procedure for the efficient production of large quantities of recombinant AAV vectors would clearly be highly beneficial.

SUMMARY OF THE INVENTION

The present invention seeks to overcome these and other drawbacks inherent in the prior art by providing novel compositions and methods for use in the efficient, large-scale production of recombinant adeno-associated virus (AAV). The compositions of the invention include recombinant AAV vectors, AAV-producing cell lines including such vectors, and recombinant infective virus vectors capable of expressing essential AAV genes required for AAV virion assembly and genome packaging. The invention also provides advantageous methods for AAV production which utilize virus infection and do not require DNA transfection.

The following terms and definitions employed herein to refer to recombinant adenoviruses and AAV inserts follow the conventional type of nomenclature used in the art. AdAAV is used as a general term to refer to adenovirus that contains one or more AAV genes inserted in any region of the adenovirus genome, this includes replication defective and replication competent adenovirus. Adenovirus carrying a particular gene can be termed as a prefix, Ad-, when the letters representing the inserted DNA will follow the prefix. The location in the adenovirus where the exogenous DNA is inserted will be a suffix, such as -E1 or -E4. For example, AdAVlacE1 is recombinant adenovirus carrying an AAV-lacZ DNA inserted in the E1 region.

The AAV rep-lip-cap gene is abbreviated as rc, the rep-lip gene is abbreviated as rep, and the cap gene is represented as cap. Therefore, AdcapE3 is the cap gene of AAV inserted into the E3 region of an adenovirus. The ITR sequences are the only essential cis-acting elements for an AAV vector to mediate genome packaging and integration into host cells. The presence of ITRs in a DNA fragment will be indicated by "AV". For example, AVlac is a DNA fragment contains two ITR sequences flanking a lacZ gene. Such a DNA fragment is also referred as an AAV vector.

In first embodiments, the invention concerns novel virus constructs including essential AAV genes and recombinant infective virus particles or virions including such DNA constructs. The recombinant virus containing the novel constructs will be virus capable of infecting mammalian cells, with preferred examples being vectors and virions of the adenovirus or herpes virus families. Recombinant viral constructs of the invention will generally be adenoviral or herpes virus vectors capable of expressing essential AAV proteins, i.e., constructs containing a recombinant insert or inserts which include one or more expression regions encoding one or more essential AAV proteins. Such recombinant inserts capable of expressing essential AAV protein(s) may also be termed "transcription units".

Adenovirus used in this invention may be from any of the 42 different known serotypes or subgroups A–F of adenovirus, with Adenovirus type 5 of subgroup C being preferred as this is the most commonly used in the art. In addition, other viruses which are capable of serving as helper viruses for AAV replication and which are capable of receiving an AAV insert may be employed. Viruses belonging to the herpes family or class of viruses are particularly contemplated as they naturally provide AAV helper functions and can be readily engineered to express essential AAV proteins. Therefore, the term "herpes virus" is used in this context to particularly refer to herpes simplex virus (HSV), Epstein-Barr Virus (EBV), cytomegalovirus (CMV) and pseudorabies virus (PRV).

As used herein, the terms "essential AAV genes" and "essential AAV protein" are intended to refer to those genes, and their encoded proteins, which are normally encoded by wild type AAV and are required for AAV replication, genome packaging and virion assembly. Naturally, when intended for use in AAV production, the adenoviral or herpes virus vector will be constructed so the inserted AAV genes complement any essential AAV genes which have been deleted from a recombinant AAV vector to allow an exogenous gene, such as a therapeutically important gene, to be inserted into the AAV vector.

Generally speaking, the adenovirus and herpes virus vectors and recombinant virions will therefore incorporate inserts with expression regions which comprise one or more of the AAV rep, lip and cap genes, and in certain preferred embodiments, will include all three of these genes. The recombinant inserts may also include other AAV sequences, but those vectors which include essential AAV genes and which lack other AAV sequences, such as, e.g., full length AAV inverted terminal repeat (ITR) sequences, will be most preferred. Infective virions expressing one or more essential AAV genes may be employed to supply these genes, and consequently, the rep, lip and/or cap proteins, to cells containing a recombinant AAV vector in which the particular essential gene or genes have been replaced by a chosen DNA segment or transgene.

Essential AAV genes may be introduced into recombinant adenovirus or herpes virus in accordance with the invention simply by inserting or adding the AAV coding sequences into the viral genome. However, more generally, an adenovirus or herpes virus gene will be deleted and the essential AAV coding sequence(s) will be introduced in its place. Any genes, whether essential for replication, such as adenovirus regions E1, E2 and E4, or non-essential for replication, such as adenoviral E3, may be deleted and replaced in this manner. Where the deleted gene is essential for replication, the resultant recombinant virus will be a replication-deficient adenovirus or herpes virus vector capable of expressing an essential AAV protein. Techniques for preparing replication-defective infective viruses are well known in the art, as exemplified by Ghosh-Choudhury & Graham (1987); McGrory et al. (1988); and Gluzman et al. (1982), each incorporated herein by reference.

Replication-defective viral vectors in accordance with the present invention will generally be constructed by deleting or removing a gene required for adenovirus or herpes virus replication and introducing in its place the desired AAV genetic material. Where this approach is taken, any gene required for adenovirus or herpes virus replication may be deleted and replaced by an essential AAV gene or genes. Suitable examples include, for instance, replacement of the adenovirus E1, E2 or E4 genes; insertion into the HSV tk gene; insertion into the PRV tk, gIII or gX glycoprotein genes; and insertion into CMV α- or $\beta_{2.7}$ promoter regions. Replacement of the adenovirus E1 gene is preferred in certain embodiments as this procedure is most routinely practiced in the art, however, replacement of the adenovirus E4 gene is preferred in certain other embodiments as this is contemplated to allow for particularly high titre AAV production when combined with E4 expressing cells.

The adenoviral or herpes virus vectors of the invention may direct the expression of AAV gene or genes by using either 'natural promoters', i.e., adenovirus or herpes virus promoters, or 'heterologous promoters', i.e., promoters from other sources. The choice of promoter is not believed to be particularly critical so long as the promoter effectively directs the expression of the AAV gene or genes. One may also use a constitutive promoter to ensure a high, constant level of expression of the AAV genes.

The promoter used may be from any viral or eukaryotic source, including plant and animal promoters, such as those in the following exemplary list. Promoters derived from plant and animal genes may include promoter sequences from significantly expressed genes, such as the α-tubulin gene and β-actin genes in plants and, by way of example, the immunoglobulin and hormone genes in animals.

Preferred promoters for use in accordance herewith include viral promoters, such as the SV40 late promoter from simian virus 40, the Baculovirus polyhedron enhancer/promoter element, Herpes Simplex Virus thymidine kinase (HSV tk), the immediate early promoter from cytomegalovirus (CMV) and various retroviral promoters including LTR elements. For simplicity, the use of AAV promoters, such as the AAV P5 promoter, will generally be preferred in most cases. The vectors of the invention will also generally include a polyadenylation signal. Any suitable signal may be employed, but AAV sequences such as the AAV common polyadenylation signal are preferred.

In certain embodiments, particularly preferred vectors are replication-defective adenoviral or herpes virus vectors which include the AAV rep, lip and cap genes, along with the AAV P5 promoter and the AAV common polyadenylation signal. In other preferred embodiments, the invention provides replication-competent adenovirus vectors in which the rep-lip gene, the cap gene, or the entire rep-lip-cap unit is inserted in place of the E3 region (Adrep3, Adcap 3 and Adrc3, respectively).

In distinct embodiments, the present invention also encompasses novel virus constructs including recombinant AAV vectors and recombinant infective virions including such DNA constructs. These type of recombinant viral constructs and virions will generally be adenoviral or herpes (HSV, PRV and CMV) virus vectors and virions which have a DNA insert including an AAV vector which itself contains a recombinant insert encoding a chosen DNA segment, such as an exogenous gene or 'transgene'. This is exemplified herein by the construction of pXAVlac containing the well-known marker gene lac-Z. However, any DNA segment or gene may be employed as a transgene in this regard, providing the length of the DNA segment does not significantly exceed about 5 kb in length. As with the first described vectors and viruses, ones bearing AAV vectors may also be either replication-defective, such as pXAVlac, or replication-competent, such as those in which the AAV vector is inserted into adenovirus E3, e.g., those based upon the plasmid pFGdX1.

The terms "transgene" and "transgenic" most often refer to an exogenous gene which has been introduced, generally, by the hand of man, into a host cell or host animal. In this sense, therefore, an exogenous DNA segment is not strictly 'a transgene' whilst it still resides within the AAV vector, rather it may properly be referred to as a recombinant DNA segment or recombinant gene. However, as AAV virions including such recombinant DNA segments are intended for use in connection with host cells and, ultimately, with host animals, the recombinant genes will later become 'transgenes' when introduced into such cells. In this sense, for simplicity, AAV vectors with recombinant DNA inserts may be termed "transgenic" AAV vectors.

Recombinant, transgenic viruses and virions in accordance with this aspect of the invention may be employed to infect cells as a means of introducing recombinant AAV vectors into the cells, and preferably, to provide a stable copy of the AAV-transgene sequence which may be subsequently rescued when supplied with essential AAV functions, such as rep, lip and/or cap. The stable AAV-transgene copies may be integrated into the host cell genome or may be maintained as an episome.

In preferred embodiments, the AAV vectors described above will be non-replicative, recombinant or transgenic AAV vectors. A "non-replicative, recombinant or transgenic AAV vector" is an AAV vector which includes a recombinant insert encoding a desired protein, which vector is capable of integrating into a host cell genome but is incapable of directing its own replication and viral packaging. Such vectors will generally comprise AAV inverted terminal repeat (ITR) sequences along with an expression region encoding a recombinant protein. These vectors may also be functionally described as AAV constructs which are capable of replication when complemented in trans by the appropriate essential AAV genes.

Further aspects of the present invention concern a variety of recombinant host cells. As used herein, the terms "recombinant" or "engineered" cells are intended to refer to cells into which a recombinant or exogenous DNA segment or gene has been introduced through the hand of man, such cells are distinguishable from naturally occurring cells which do not contain a recombinantly introduced exogenous DNA segment or gene. The recombinant host cells of the present invention will be cells which incorporate adenoviral or herpes virus vectors capable of expressing essential AAV proteins. In preferred embodiments, the vector will be introduced into the host cell by infection with recombinant virus.

Virtually any cell is considered to be suitable for use as a host cell in accordance with the present invention, with cells which are readily susceptible to infection by adenovirus or herpes virus being particularly preferred. Host cell lines are generally selected for known technical criteria such as ease of growth without complex media requirements and maintenance of inserted DNA. Useful cell lines are contemplated to include, for example, HeLa cells, KB cells, JW-2 cells, Detroit 6 cells, COS cells, CV-1 cells, VERO cells, NIH-3T3 cells and the like. Such cells are commonly available, e.g., commercially available through the American Type Culture Collection (ATCC). One example of a particularly suitable host cell which is routinely used in the art is a 293 cell (transformed primary human embryonal kidney cells).

More preferred recombinant host cells will be those which further include a stable recombinant AAV vector containing a gene of interest. "Stable" in this context means that the AAV vector sequences reside and are maintained in a host cell, such as by being integrated into the genome, i.e., integrated into a host cell chromosome, or maintained as an episome. In certain embodiments, the most preferred cells will be those cells in which a non-replicative, recombinant AAV vector including ITR sequences and a gene or DNA segment of interest, is integrated into the genome of the cell.

The generation of recombinant AAV vectors themselves is well known to those of skill in the art. In general, the desired DNA may be ligated into the AAV genome in place of or in addition to the cap, lip or rep genes or in place of or in addition to any AAV DNA sequence excluding the first and last 145 base pairs, as described in U.S. Pat. No. 5,139,941, incorporated herein by reference. Although U.S. Pat. No. 5,139,941 describes inefficient methods for initial AAV generation, i.e., those relying on transfection, it does disclose how to make recombinant AAV vectors comprising foreign DNA suitably ligated into the AAV genome. In preferred embodiments, it is contemplated that the AAV vectors most suitable for use in accordance herewith will have exogenous DNA inserted in place of one or more of the rep, lip and cap genes, and most preferably, in place of all three such genes. Of course, the present invention is not limited to any specific exogenous gene or DNA segment, and it is contemplated that virtually any gene that one desires to insert would be suitable, so long as it is not prohibitively long, i.e., significantly longer than about 5 kb.

Recombinant host cells which include recombinant AAV vectors capable of rescue, i.e., having the potential to produce recombinant AAV virions, are termed "AAV producer cells". Preferably, producer cells of the present invention will include an AAV vector which is integrated into the genome and is capable of expressing a desired transgene. Rescue of the AAV vector will then result in the generation of recombinant AAV virions carrying the transgene, which may be employed to deliver the gene to other cells, e.g., as in gene therapy.

The "rescue process" is the process by which the producer cells are rendered capable of producing recombinant AAV virions. This is generally achieved by supplying the cell with the AAV functions needed for replication and packaging. In accordance with the preferred methodological aspects of the present invention, rescue is achieved by infecting the producer cell with recombinant adenovirus or herpes virus encoding one or more of the essential AAV functions rep, lip and cap, as required.

Accordingly, the most preferred AAV producer cells will be those comprising a stably integrated recombinant AAV vector which includes AAV ITR sequences and an expression region encoding an exogenous gene, the cell being capable of producing recombinant AAV virions when contacted with replication-deficient adenovirus or herpes virus particles which include a vector capable of expressing one or more AAV proteins essential for AAV replication, genome packaging and virion assembly.

As will be discussed in detail herein, it should be noted that the present invention encompasses methods for AAV production which do not, technically, require the prior production of a "producer cell" in the sense that this term is most commonly used in the art. These are the processes by which a host cell is simultaneously contacted with the AAV vector and the required AAV essential genes, including simultaneous transfection/infection processes and, also, double and triple infection procedures. However, the execution of such methods still, of course, results in the generation of a cell which includes a recombinant AAV vector and which is capable of producing recombinant AAV.

Further and particularly important aspects of the present invention concern novel methods for producing recombinant AAV virions, which methods are especially advantageous as they are not limited by transfection. To produce AAV virions according to the methods of the present invention, one would generally introduce into a host cell a recombinant AAV vector, and infect the cell with recombinant adenovirus or herpes virus capable of expressing one or more essential AAV proteins, i.e., those required for replication, packaging and assembly. Then one would culture the cell under conditions and for a period of time effective to allow the cell to produce recombinant AAV virions. The process of "introducing into a host cell a recombinant AAV vector" may be the process by which a producer cell is formally created, as described above, or it may be a simultaneous transfection/infection or double or triple infection process, as described below.

In preferred embodiments, the AAV production methods of the invention involve, first, preparing a recombinant adenovirus or herpes virus which includes a vector construct capable of expressing an essential AAV protein and, second, preparing a cell capable of producing AAV by introducing a recombinant AAV vector into a host cell. The AAV vector will preferably be a non-replicative, recombinant AAV vector including AAV ITR sequences and a transgene of interest which is capable of being stably maintained by the cell. One would infect this cell with the recombinant virus in an amount effective to stimulate the production of recombinant AAV virions, and culture the infected cell to obtain the virions so produced.

The preparation and purification of recombinant AAV virus is described in U.S. Pat. No. 5,173,414, incorporated herein by reference. Although the methods for initial AAV production described in U.S. Pat. No. 5,173,414 rely on transfection, and are therefore inefficient, this reference teaches how to prepare AAV, i.e., how to "harvest" the virus from cells capable of producing AAV. Further suitable methods for harvesting the virus will be known to those of skill in the art in light of the present disclosure and articles such as, for example, Samulski et al. (1987). Adenovirus may be removed by any suitable techniques, including heat inactivation, CsCl gradient sedimentation or chromatographic techniques.

The cell capable of producing AAV may be supplied with essential AAV proteins by infection with any one of, or a combination of, a variety of recombinant infectious viruses. For example, a single virus which may employed which includes a vector construct expressing the AAV rep, lip and cap genes. Alternatively, one recombinant virus which includes a vector expressing the AAV rep-lip genes may be used in conjunction with a second recombinant virus including a vector expressing the AAV cap gene. In either case, the AAV genes may be introduced at any point of the adenovirus or herpes virus.

The recombinant infective virus used in accordance herewith may be adenovirus, HSV, PRV, CMV and the like, and may be either a replication competent virus or a replication-defective virus, such as a replication-defective adenovirus. Such viruses will generally be replication-defective as a result of deleting essential genes in order to create space for an essential AAV gene or genes be inserted. Where replication defective viruses are employed, the defect may be complemented by using an AAV-producing cell which directly expresses the protein or proteins required. Alternatively, the AAV-producing cell may be infected with a second, or even a second and third recombinant virus, which complements the defect.

By way of example, one may replace the E1 region of an adenoviral construct with a recombinant insert including the AAV rep, lip and cap genes or any one of such genes. To complement this virus, one may use a producing cell which expresses E1, such as an E1-expressing 293 cell, or one may co-infect a cell with a second adenovirus which includes a functional E1 region. The second adenovirus may be of any type so long as it directs the expression of E1 proteins. It may be one in which other functional units, including essential AAV genes or selected transgenes, have been introduced into regions such as the E3 or E4 regions.

The combination of viruses and AAV producing cells is, of course, not limited to E1-lacking virus and E1-expressing cells. Indeed, any complementary combination of viruses and host cells may be employed in connection with the present invention. For example, where the recombinant virus lacks functional E2, an E2-expressing cell or second virus may be used, where the recombinant virus lacks functional E4, an E4-expressing cell or second virus will be effective, and the like. Where a gene which is not essential for replication is deleted and replaced, such as, for example, the E3 gene, this defect will not need to be specifically complemented by the host cell.

In complementing the replicative defect of an infective virus by co-infection with another virus, the use of E3-lacking recombinant adenovirus is particularly preferred. For example, recombinant adenovirus which bear AAV genes in place of the E3region may be used in combination with recombinant adenovirus that carry an AAV transgenic vector in place of the E1 gene. This allows high levels of AAV to be produced without need of special cell lines and is advantageous in that it renders the lower level of E1 protein expression in cell lines, such 293 cells, of little consequence.

The present invention encompasses four broad methods for preparing AAV virions based upon the virus and AAV-containing cell compositions described above. In all these methods the most preferred AAV vector will be a non-replicative, recombinant AAV vector including AAV ITR sequences and a gene of interest which is capable of integrating into the host cell genome on introduction. The methods encompassed by the invention are variations based upon the method of initially introducing an AAV vector into a cell in order to create a cell capable of producing AAV.

In a first example, a typical AAV producer cell is prepared by transfecting a host cell with the chosen recombinant AAV vector, this may be referred to as "prior introduction". This may be achieved by any suitable physical or chemical method, such as, for example, $Ca^{2+}$-, liposome-or protein conjugate-mediated transfection, via electroporation, or indeed, via any other known method. In a second example, the cell capable of producing AAV is formed by transfecting a cell with an AAV vector and, at the same time, infecting the cell with recombinant adenovirus or herpes virus expressing essential AAV proteins, this may be referred to as "simultaneous introduction". In this method, the infectious virus will generally also promote the efficient transfer of the AAV vector, particularly as it helps vector DNA escape from lysosomes.

In a third example, termed "double infection", a cell is simultaneously infected with two forms of recombinant adenovirus or herpes virus, one of which will express essential AAV proteins, and the other which will include a non-replicative, recombinant AAV vector encoding a desired protein and capable of integrating into the genome. A further variation of this is the fourth example which may be termed the "triple infection" method. In this method, cells are infected with three forms of recombinant adenovirus or herpes virus, the combination of which results in the expression of all the essential AAV proteins and also provides the non-replicative, AAV vector encoding the desired protein.

In double and triple infection methods, the most preferred combinations are those in which the AAV genes and the AAV vector are inserted at different regions of the recombinant adenoviruses. This is exemplified by using AdAV-lacE1 with AdrcE4, AdAVlacE1 with Adrc3 or AdAVlacE1 with AdrepE3/AdcapE3. In these cases, when the adenoviruses co-infect the host cells, their defects are complemented by each other. Also, as AdrepE3, AdcapE3 or Adrc3 will direct the production of E1, the above combinations of constructs may be used in methods to produce recombinant AAV using any cells that are susceptible to adenovirus infection, such as BK or HeLa cells, and are not limited to E1-expressing cell lines.

Further aspects of the present invention concern recombinant AAV virions and virus stocks prepared by any of the methods described herein and pharmaceutical compositions comprising such recombinant AAV virions in pharmacologically-acceptable formulations. The pharmacologically-acceptable vehicles may be buffered saline solutions rendered essentially free of undesirable contaminants, such as adenovirus particles or endotoxins and other components which may cause untoward reactions in a recipient animal or individual.

The recombinant AAV vectors of the invention and the virions produced by methods in accordance with the invention may include any desired DNA segment or gene, with the general limitation that it be of about 5 kb in length or less, or preferably about 4.7 kb in length or less, to allow effective packaging into virus particles. Apart from the size considerations, it will be understood that the invention does not limit in any way the choice of the exogenous DNA segment or gene. DNA from any source may be employed, and both coding and anti-sense constructs may be used. The recombinant AAV may be employed in any one of a variety of embodiments, such as, e.g., in introducing a desired gene into a cell in vitro, or used as a delivery vehicle for gene therapy in vivo wherein sense, or antisense, genetic constructs are delivered to cells within an animal, such a human subject.

In still further embodiments, the invention concerns AAV vector constructs comprising a full length cystic fibrosis transmembrane conductance regulator (CFTR) gene which are capable of expressing the entire CFTR protein, recombinant AAV virions including such CFTR constructs, pharmacologically-acceptable formulations of such AAV virions, and methods for their preparation and use. Although the invention is clearly not limited to aspects connected with the CFTR gene, it does, in further exemplary embodiments, provide methods for treating cystic fibrosis. Such methods generally comprise administering to a mammal with symptoms of cystic fibrosis an effective amount of a pharmacologically-acceptable composition comprising recombinant AAV virions which include a recombinant AAV vector construct capable of expressing the entire CFTR protein. The animals treated in this manner may generally be any mammal suspected of having mutations within the CFTR gene, including, of course, human subjects.

BRIEF DESCRIPTION OF THE DRAWINGS

FIG. 4(points A–B). Southern Blot analysis of AdAAV (AdrcE1). FIG. 4 consists of FIG. 4A and FIG. 4B on a single page. Viral DNAs of AdrcE1 and the parental virus, AdΔE3, were isolated and digested with the XbaI restriction enzyme. The plasmid, SSV9, was also cut with XbaI to generate the 4.4 kb rep-lip-cap DNA fragment. All three DNA samples were loaded onto a 0.8% agarose gel. After electrophoresis, DNAs were transferred to a nylon membrane and hybridized with a mixture of $^{32}$P-CTP-labeled DNA probes specific to the rep and cap sequences. After a series of washes of the nylon membrane in 0.5×SSC at 68° C., the membrane was exposed to an X-ray film (Dupont). The photograph of the agarose gel before transferring the DNA to a nylon membrane is shown in FIG. 4A, and the autoradiograph of the Southern Blot is shown in FIG. 4B.

FIG. 6. Demonstration of AAV production using recombinant adenovirus that carries the AAV genes. FIG. 6 consists of FIG. 6A and FIG. 6B on a single page. 293 cells were transfected twice with pAVcmvlac (an AAV vector containing a LacZ gene in a CMV transcription unit) using Lipotransfectamine (Gipco & BRL) and infected with AdrcE1 (an AdAAV) and 10% of wild type Ad5. Three days post transfection, the cells were lysed and sonicated for 10 seconds. After removal of the cell debris by low speed centrifugation, the supernatant was used to infect HeLa cells. At 24 hours post transfection, the cells were fixed with 0.3% glyceraldehyde and stained with X-Gal. Photos were taken under an inverted light microscope.

DETAILED DESCRIPTION OF THE PREFERRED EMBODIMENTS

Figure 1:
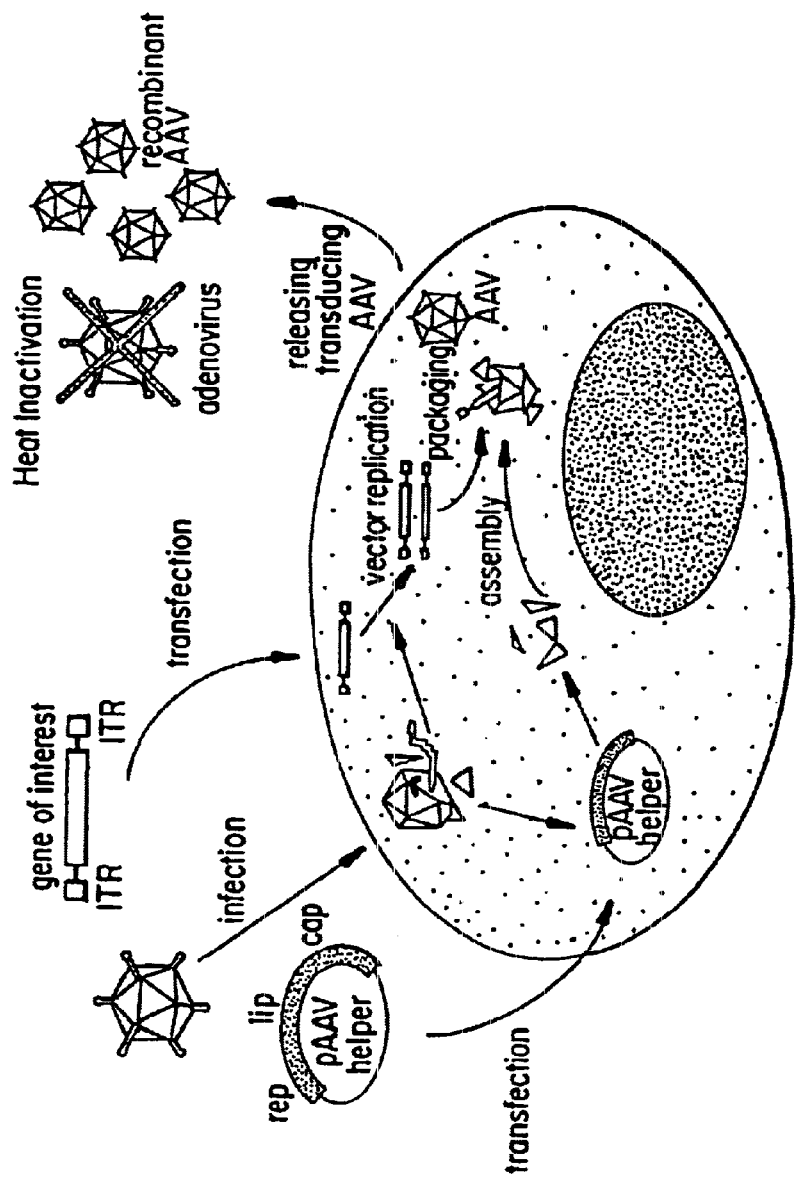
FIG. 1. A schematic diagram of the standard (prior art) method used for the production of transducing AAV virions prior to the present invention. An AAV vector and a helper plasmid that contains the AAV genes (rep-lip-cap) essential for replication are co-transfected into cells that have been infected with adenovirus. Factors from adenovirus will activate synthesis of AAV proteins for AAV assembly, and permit the replication of the AAV vector. The AAV vector will then be packaged into transducing AAV virions and released into the medium along with adenovirus. Adenovirus can be either heated inactivated or removed by CsCl gradient sedimentation, or by chromatography.

In recent years, gene therapy has been proposed as a method for treating a variety of genetic disorders which lack fully effective therapies. Some of the most likely disease candidates for gene therapy treatment include genetic diseases of the blood, such as sickle-cell anemia, clotting disorders, and thalassemias, inherited immune deficiency syndrome (ADA deficiency) and cystic fibrosis. Gene therapy may also prove useful in the treatment of cancer, diabetes, AIDS, hypercholesterolemia, other disorders of the liver and lung and diseases associated with hormone deficiencies.

Gene Therapy Techniques

Successful gene therapy generally requires the integration of a gene able to correct the genetic disorder into the host genome, where it would co-exist and replicate with the host DNA and be expressed at a level to compensate for the defective gene. Ideally, the disease would be cured by one or a few treatments, with no serious side effects. There have been several approaches to gene therapy proposed to date, but each suffer from their particular drawbacks.

A first approach is to transfect DNA containing the gene of interest into cells, e.g., by permeabilizing the cell membrane either chemically or physically. This approach is limited to cells that can be temporarily removed from the body and can tolerate the cytotoxicity of the treatment (i.e. lymphocytes). Liposomes or protein conjugates formed with certain lipids and amphophilic peptides can be used for in vivo transfection (Stewart et al., 1992; Torchilin et al., 1992; Zhu et al., 1993), but the efficiency of gene integration is very low. It is estimated that the gene of interest integrates into the genome of only one cell in 1,000 to 100,000. In the absence of integration, expression of the transfected gene is limited to several days in proliferating cells or several weeks in non proliferating cells due to the degradation of the un-integrated DNAs. This makes a transfection approach sub-optimal.

A second approach capitalizes on the natural ability of viruses to enter cells, bringing their own genetic material with them. Retroviruses have promise as gene delivery vectors due to their ability to integrate their genes into the host genome, transferring a large amount of foreign genetic material, infecting a broad spectrum of species and cell types and of being packaged in special cell-lines (Miller, 1992). However, two major problems hamper the practical use of retrovirus vectors. First, retroviruses only integrate efficiently into replicating cells and, second, they are difficult to concentrate and purify.

A third method uses DNA viruses, such as adenovirus, which are engineered to serve as vectors for gene transfer. But many DNA viruses that can accept foreign genetic material are limited in the number of nucleotides they can accommodate and in the range of cells they infect. Moreover, adenoviruses do not integrate their genetic material into the host genome and therefore expression is transient necessitating repeated exposures. The limited serotypes of the adenovirus currently available for vector development and host immunity pose limitations on repetitive administration.

Another limitation on adenovirus vectors is the difficulty of eliminating viral genes from the vector. This means that recipient cells will not only express the therapeutic gene but will also express at least a low level of viral proteins (Gregory et al., 1992; Rosenfeld et al., 1992), attracting immune responses against the transduced cells that cause inflammation in the recipient organ. The co-transfer of viral genes into recipient cells also opens the possibility that the defective viral genome can be rescued by a wild-type virus infection which provides the essential viral genes deleted from the vector. This poses the danger of spreading the genetically engineered gene among the normal population. Furthermore, studies have shown that recombinant adenovirus which are meant to be replication-defective can in fact replicate slowly (Shenk et al., 1980), raising general safety concerns.

Cystic Fibrosis (CF)

Of the more than 4,000 known genetic disorders most lack fully effective therapies. Cystic fibrosis (CF) is one of these devastating diseases, having a high incidence in Caucasian populations. The principal manifestations of CF include thickened exocrine gland secretions, pancreatic deficiency, intestinal blockage and malabsorption of fat. By far the most serious factor affecting mortality is the chronic lung disease. Therefore correction of the defect in the lung would become the first priority of a gene therapy regimen.

The gene responsible for this disease was isolated by Tsui, Riordan, Collins and co-workers using reverse genetics in 1989 (Riordan et al., 1989). It encodes a protein called the cystic fibrosis transmembrane conductance regulator (CFTR) which is involved in the transfer of chloride ions (Cl⁻) through epithelial cell membranes. Evidence from functional studies implies that mutations in this gene result in defects of Cl⁻ secretion in epithelial cells which may cause the various clinical manifestations. Therefore, it is of great interest to restore the functions of CFTR by introducing a copy of the functional gene into affected cells in vivo.

Restoration of the cAMP-stimulated Cl⁻ transport in in vitro complementation studies has been achieved (Drumm et al., 1990), although there has not been direct evidence that this could be achieved in vivo. The AAV-mediated gene transfer protocols made possible by the large-scale AAV production methods of the present invention will now enable the transfer of the CFTR gene into animals with CF. It is envisioned that CFTR gene transfer will reduce or eliminate the pathological progression of cystic fibrosis.

Adenoassociated Virus (AAV)

The present inventors contemplate that Adenoassociated Virus (AAV) is the most suitable candidate for use as a vector in gene therapy, and is particularly suitable for cystic fibrosis treatment. Although AAV is also a member of DNA viruses it retains several properties not shared by the other members of the DNA viruses. Like retroviruses, AAV integrates its genome into the host DNA upon infection (Kotin et al., 1990; Samulski et al., 1991). This process is catalyzed by viral protein and is mediated by the inverted repeat that flanks the viral genes at each end of the genome. This will ensure the complete integration of the genetic material inserted between the inverted repeats. Importantly, unlike retroviruses the integration of AAV DNA into the cellular genome appears to be independent of cell replication. This makes it a suitable vector for gene delivery into airway since the majority of the cells are quiescent.

Other advantages of AAV based vectors include the fact that AAV is not associated with any disease (Ostrove et al., 1981; Cukor et al., 1984) and that AAV virions are resistant to physical treatments, such as sonication and heat inactivation, that are not tolerated by other viruses during purification. Unlike retrovirus vectors, AAV vectors do not silence the transcription of the transgene (Towns, personal communication, 1993), which ensures permanent expression of the transferred therapeutic gene in the recipient cells. Also AAV infects hematopoietic stem cells (Lebkowski et al., 1988; Walsh et al., 1992) and gene expression within these cells is sustained after cell differentiation. This makes it possible to use AAV vectors to treat genetic diseases of the blood, such as sickle-cell anemia and ADA deficiency. It is also possible to transfer genes into bone marrow or peripheral blood stem cells for gene therapy of hormone deficiencies, because these cells are easy to isolate for in vitro transduction.

In addition to using recombinant AAV virions in gene transfer embodiments, AAV may also be employed in other molecular biological techniques, for example, as an expression vector. In these embodiments, the size of the DNA insert would not, of course, be limited by the packaging capacity of the AAV virions. It is known that large DNA segments (e.g., up to 20 kb) of foreign DNA can be inserted into recombinant AAV plasmids without significantly affecting the ability of the AAV recombinant genome to be activated or rescued following transfection into human cells. This means that, in the presence of helper virus, AAV plasmids can be used as transient expression vectors. Furthermore, rescue of AAV recombinants could be achieved after integration into a mammalian chromosome, indicating that AAV vectors could be used in conjunction with other DNA transfer techniques, such as, e.g., microinjection, protoplast fusion, calcium phosphate transfection and the like, to rescue foreign DNA from mammalian cells.

The range of host cells in which AAV can grow is particularly broad, and virtually every mammalian cell line which has been tried can be productively infected with AAV provided an appropriate helper virus is used (Cukor et al., 1984). The host range for AAV integration is believed to be equally broad, and to include murine cells. The wide range of cells which may used in conjunction with AAV has important implications both for in vivo and in vitro uses of recombinant AAV.

Despite the compelling advantages of AAV-based vectors for gene therapy, there are certain limitations to their practical use. In regard to gene therapy for cystic fibrosis, as the total packaging capacity of AAV virus is under 5 kb (Muzyczka, 1992), it has been difficult to achieve efficient packaging of CFTR (4.7 kb) into the AAV virion. Also, efficient gene expression from the AAV promoters depends on the activation by viral proteins made from adenovirus (Shi et al., 1991).

AAV is dependent on helper functions from either adenovirus or a range of herpes virus family viruses for its own replication. In the absence of such a helper virus, AAV will infect cells and integrate into the host genome, but will not replicate or produce new viral particles. This means that AAV is generally produced in adenovirus- or herpes-infected cells which supply the helper functions necessary for the production of new AAV viral particles. However, this does not pose a limitation to producing recombinant AAV. The more general and important problem which limits the practical use of AAV is the fact that the production methods also rely on DNA transfection, which is laborious and particularly inefficient.

In recombinant AAV, one or more of the viral genes necessary for AAV replication and virion production (cap, lip and rep) are replaced by the exogenous gene of interest. The production of recombinant AAV therefore requires these essential genes to be supplied. Current methods generally employ co-transfection of an AAV vector carrying a gene of interest, together with a helper AAV plasmid that expresses all of the essential AAV genes, into adenovirus- or herpesvirus infected cells (FIG. 1). The plasmids used for transfection have been modified to provide limited ability to replicate, but this approach still relies on transfection to introduce the plasmids into cells for AAV production and as a result the production efficiency was only increased by 10% (Page et al., 1993).

Recently, other procedures for preparing AAV virions have been reported. Lebkowsi et al. (U.S. Pat. No. 5,173, 414) describe a method using chimeric Epstein Barr/AAV plasmids which are maintained as extra-chromosomal elements in permanent cell lines. Muzyczka et al. (U.S. Pat. No. 5,139,941) describe transduced cells with AAV vectors stably incorporated into the genome. However, both of these processes still require transfection of AAV helper functions. For example, Lebkowsi et al. employ subsequent transfection with the AAV plasmid, p Bal (Example 4 of U.S. Pat. No. 5,139,941), whereas Muzyczka et al. co-transfect the recombinant AAV plasmid along with an enlarged AAV plasmid containing wild-type AAV genes (Example 2 of U.S. Pat. No. 5,139,941).

As transfection of essential AAV genes is an absolute requirement of even the most recently reported processes (e.g., U.S. Pat. Nos. 5,173,414 and 5,139,941), they therefore remain subject to all the limitations associated with transfection described above, including the inefficiencies of DNA uptake. The production of a significant quantity of AAV virions for various applications, including clinical uses in gene transfer, by the currently available methods thus remains impractical as all such methods are dependent on a transfection step.

Large-scale, Efficient Production of AAV

Described herein are novel techniques designed to eliminate the transfection step in AAV production. The methods of the present invention use instead an infection procedure for the preparation of recombinant AAV virions. This technique can be applied to the large scale production of AAV for use in a variety of embodiments, including the commercially-viable manufacture of therapeutic quantities of viral particles for gene therapy. AAV produced by these methods are, of course, not limited to clinical uses and may be employed in a variety of other embodiments including, for example, to transfer any gene or DNA segment into cells maintained in vitro.

Figure 2:
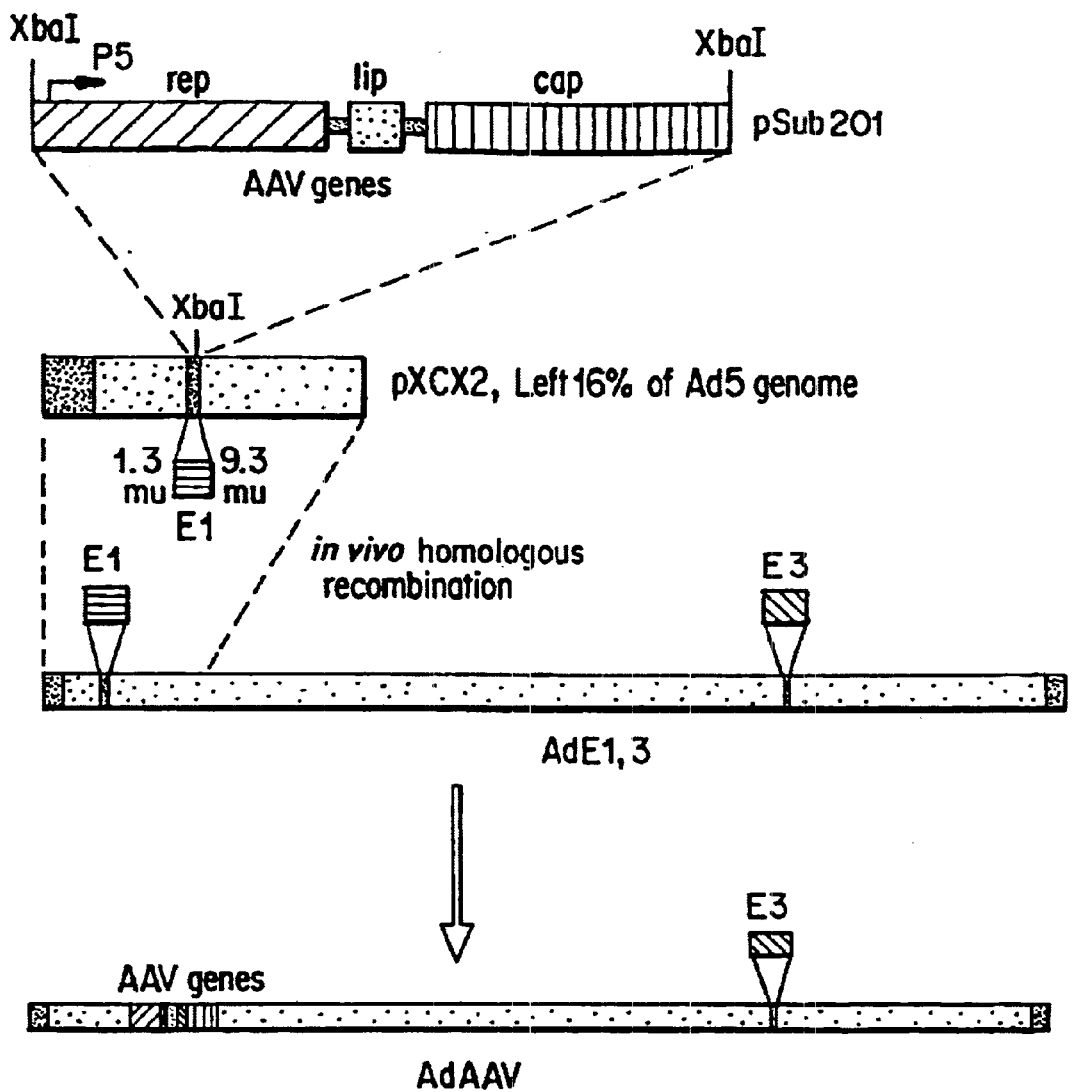
FIG. 2. A schematic diagram of the strategy for creating recombinant adenoviruses (AdAAV). The AAV genes (rep-lip-cap) without the ITR sequences are first inserted into the left portion of the adenovirus genome in place of the deleted E1 region. Recombinant adenovirus is generated by in vivo homologous recombination of the left portion of the adenovirus genome containing the AAV genes and an adenovirus genome containing deletions in both E1 and E3 regions. The resulting recombinant adenovirus genome is designated AdAAV or AdrcE1, and is shown at the bottom of the figure.
Figure 3:
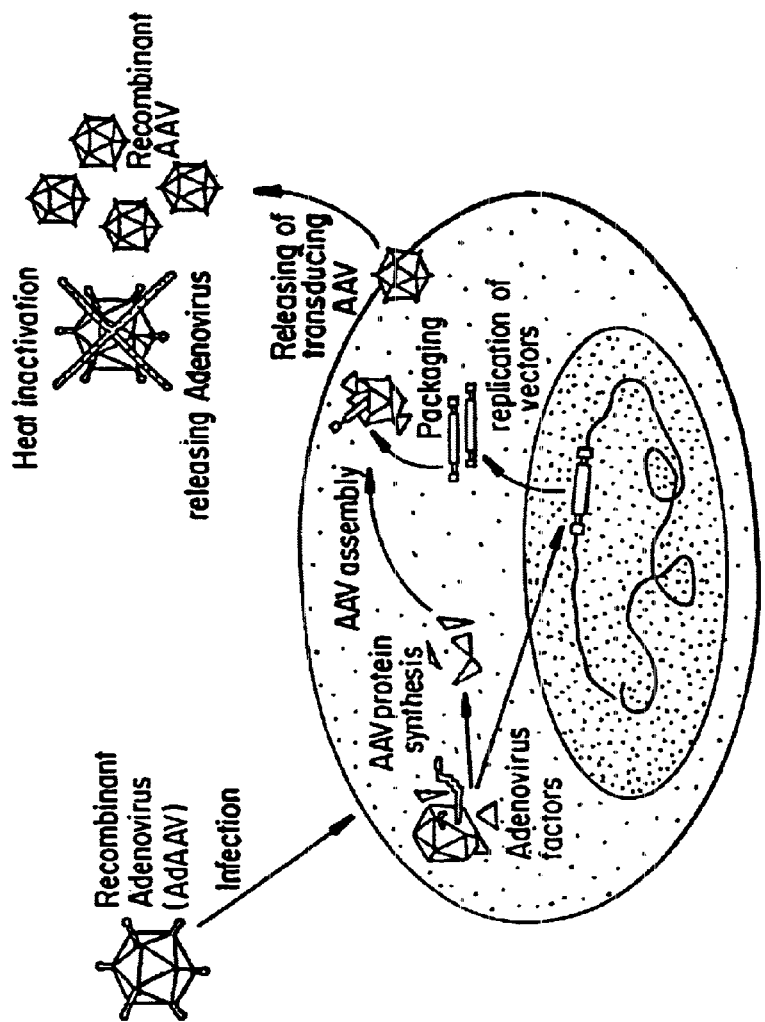
FIG. 3. A schematic diagram illustrating the production of transducing AAV virions using the new infection method of the present invention. The producer cell line contains a stably integrated AAV vector with a gene of interest. When cells are infected with the recombinant adenovirus containing the AAV genes (AdAAV), factors encoded by the adenovirus genes activate the replication of the AAV vector, which will be packaged into newly synthesized AAV virions. AAV proteins essential for replication and virion assembly are synthesized from the AAV genes carried by the recombinant adenovirus, AdAAV. In this approach, only infection of the AdAAV is required to activate the production of recombinant AAV virions, which is a very efficient process.

Certain embodiments of the procedures of the present invention are diagrammed in FIGS. 2 and 3 and may be summarized as follows. A replication-deficient, infective virus, such as a recombinant adenovirus or herpes virus, is created to express essential AAV genes required for AAV replication, virion assembly and genome packaging (FIG. 2). The viral vector will be constructed so the inserted AAV genes complement any essential AAV genes which have been deleted from a recombinant, transgenic AAV vector which one intends to produce. The virus expressing the essential AAV genes can then be employed to supply these genes to an AAV vector-containing producer cell by infection, rather than using the inefficient process of transfection. This is the first example of a method to produce recombinant AAV which is not limited by transfection.

The essential AAV genes supplied by the adenovirus or herpes virus vectors will generally be one or more of the AAV rep, lip and cap genes. When used in conjunction with an AAV vector in which all of the rep, lip and cap genes were replaced by a transgene, the infective virus vector will include all of these genes. The vectors may also include other AAV sequences, however, the use of vectors which include the essential AAV genes but which lack full length AAV inverted terminal repeat (ITR) sequences is generally preferred.

The recombinant virus for use in accordance herewith, such as an adenovirus or herpes virus, will generally be a replication deficient virus, as exemplified by the adenovirus construct termed AdAAV. This means that the virus provides all of the adenoviral factors required for adenovirus replication except one, which deficiency must be must be complemented for in the production process. In one particular example, an AdAAV construct is rendered replication-defective through deletion of the viral early region 1 (E1A) so that the virus is competent to replicate only in cells, such as human 293 cells, which express adenovirus early region 1 genes from their cellular genome. Using such 293 cells as producer cells will complement the deficiency by providing the necessary E1 protein.

In the present example, the essential AAV genes may be most conveniently introduced into the region from which the E1 coding sequences have been removed. The E1-expressing producer cells will be cells that contain a stably integrated AAV vector which bears a gene of interest instead of the essential AAV genes. Infection of AdAAV into these producer cells results in the generation of large amounts of transducing AAV virions. Since adenovirus (in this case, AdAAV) can be produced at a very high titer ($10^9$ to $10^{12}$ PFU/ml) and can infect cells at a high efficiency, it is feasible to infect unlimited numbers of producer cells for the production of recombinant AAV virus.

It will be understood that the position at which the AAV genes are inserted into the infectious viral vector is not critical to the invention. They may thus also be inserted in lieu of a deleted E3 region, in E3 replacement vectors as described previously by Karlsson et al. (1986), or in place of E4 regions or any other essential region. Naturally, one will choose a particular cell line in light of the vector employed. That is, one will employ a cell line that is permissive for conditional replication-defective virus infection, and expresses the virus gene product "in trans" to complement the defect of the original vector. The cells may be propagated either on plastic dishes, in attached culture or in suspension culture, as is known to those of skill in the art.

Figure 7:
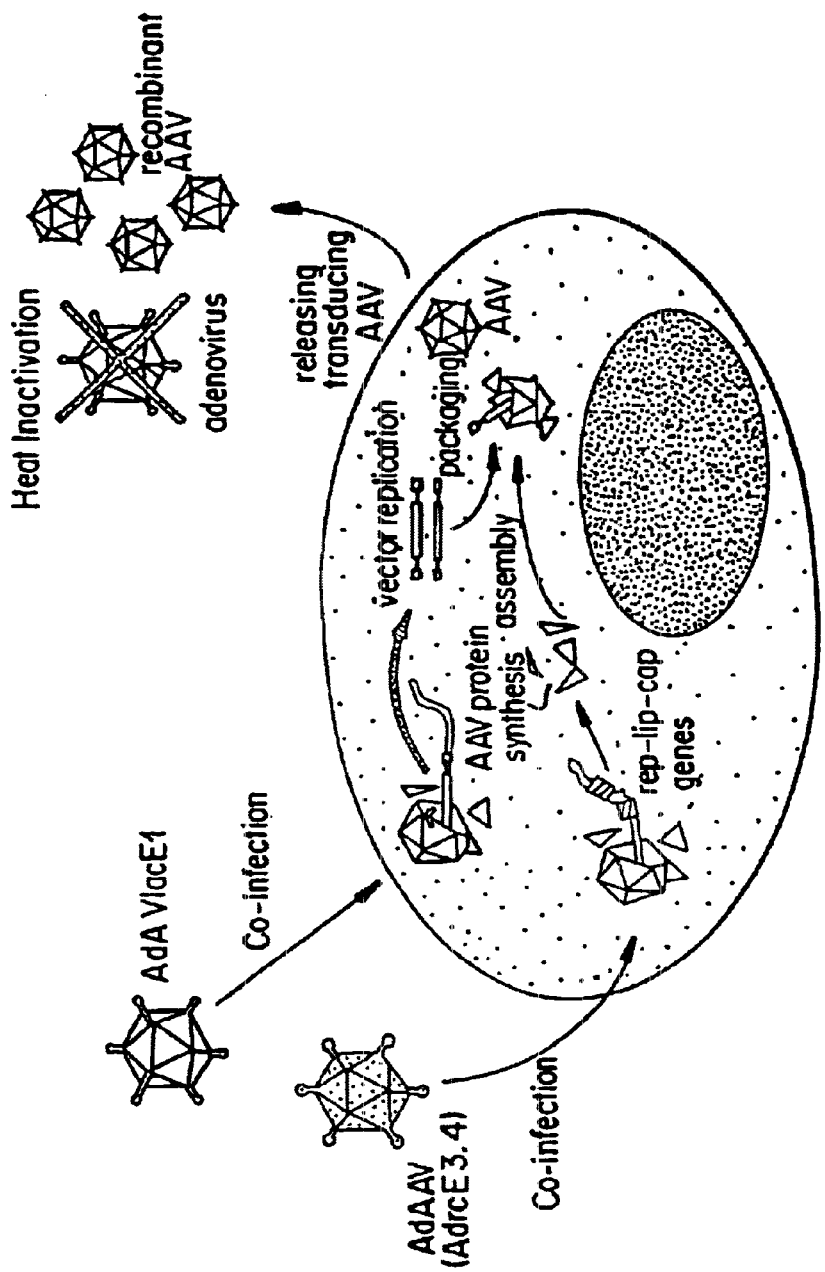
FIG. 7. A schematic diagram illustrating the production of transducing AAV virions using the double infection method. The essential genes of AAV (rep-lip-cap) and an AAV vector containing a gene of interest (lacZ gene) are carried by two recombinant adenoviruses, AdAAV and AdAVlacE1 respectively. Cells infected with both of the recombinant adenoviruses will acquire all the essential genes to produce recombinant AAV virions. AdrcE3.4 will provide all the AAV genes, rep-lip-cap and adenoviral factors, such as E1 proteins for AAV virion assembly genome replication and packaging. AdAVlacE1 will introduce the AAV vector which contains the gene of interest into the host cell, and provide the E4 protein which has been depleted from the AdrcE3.4 adenovirus. Using this approach, no special cell lines are required and high titers of recombinant AAV can be produced using any cell type that is susceptible to adenovirus infection.

Other embodiments of the present invention concern double or triple infection methods for producing AAV, as represented in FIG. 7. In these methods, a cell is simultaneously infected with two, or even three, forms of recombinant adenovirus or herpes virus. This combination results in the expression of all the essential AAV proteins and also provides the non-replicative AAV vector encoding the desired protein.

The double and triple infection methods also have the advantage that they can be utilized so that the vectors complement each other, rather than relying on the cell line to complement any replication deficiency. For example, AdAVlacE1 may be employed with either AdrcE4, Adrc3 or even AdrepE3/AdcapE3. In these cases, as AdrepE3, AdcapE3 or Adrc3 directs the production of E1, the above combinations of constructs can be used with any cell that is susceptible to adenovirus infection. These methods are therefore not reliant on using E1-expressing cell lines, such 293 cells, in which the E1 levels are lower than in adenovirus infected cells.

The nature of the adenovirus or herpes family virus is also not believed to be crucial to the successful practice of the invention. For example, any of the 42 different known serotypes or subgroups A–F of adenovirus may be used. In certain cases, Adenovirus type 5 of subgroup C may be preferred because Adenovirus type 5 is a human adenovirus about which there is significant amount of biochemical and genetic information known, and which has historically been used for most constructions employing adenovirus as a vector.

Where one desires to use a virus of the herpes virus family, many from this broad group are also available. The herpes family includes herpes simplex virus (HSV), cytomegalovirus (CMV), pseudorabies virus (PRV) and Epstein-Barr Virus (EBV) (Bauer & Monreal, 1988; Buller & Rose, 1978; Hogan et al., 1972; McPherson & Rosenthal, 1985; Parks et al., 1967), any one of which can be engineered to express essential AAV genes in accordance with the present invention (Meignier et al., 1987; Hikada et al., 1989; Keller et al., 1986). HSV, CMV, PRV and EBV all express helper proteins that are essential for AAV replication and all contain non-essential genes, or genes that may be deleted and complemented in trans, into which AAV genes can be inserted (see Example VI).

To prepare recombinant AAV in accordance with certain aspects of this invention, one may make an AAV producer cell line. It will be understood that the terms "producer cell" and "producer cell line" in context of the present invention have no relation to those producer cells used in connection with retroviruses. In certain embodiments, the creation of a "producer cell" in the strictest sense of the word is not necessary. However, a cell capable of producing AAV always results during the procedures of the invention, whether it is created in advance or created simultaneously with infection.

Both producer cells and cells capable of producing AAV are recombinant host cells which include recombinant AAV vectors capable of subsequent rescue, i.e., cells having the potential to produce recombinant AAV virions. The AAV vectors are preferably those capable of being integrated into the genome or maintained as an episome, and will, generally, include a transgene, such as a therapeutically important gene. These cells can then be used to generate recombinant AAV virions carrying the transgene, which process may also be termed 'rescue of the AAV vector'.

The AAV vector, and the recombinant AAV ultimately produced, may contain virtually any exogenous DNA segment or transgene with relatively few limitations. In general though, the inserted DNA should not exceed 5000, or more ideally, 4700 base pairs. The two terminal repeats (origins of replication) of AAV will generally be present in the recombinant AAV construct so that it may integrate into the host genome. Both coding and non-coding DNA may be inserted into an AAV vector as described herein. Coding DNA may be used with the ultimate intention of generating one or more desired proteins, functional protein domains, polypeptides, peptides, antigens, fragments thereof, and the like, within host cells, which themselves may or may not be located within a host animal. DNA encoding antisense RNA versions of any of the above may also be employed, e.g., for use inhibiting gene transcription or translation within a host cell.

There are four general ways to prepare a cell capable of producing AAV: (1) prior introduction of the AAV vector into the cell, i.e., making a producer cell; (2) simultaneous introduction of the AAV vector into the cell and infection with recombinant virus; (3) double infection and (4) triple infection methods in which a cell is simultaneously infected with two, or three, respectively, forms of recombinant adenovirus or herpes virus. In the third and fourth examples, combinations of adenoviruses used will be chosen so that all the essential AAV proteins and the desired recombinant AAV vector are supplied to a given host cell. In any event, once the producer cells and/or infective viruses have been established, the production of recombinant AAV is straight forward and can easily be achieved by repeated infection.

In the first two methods for preparing AAV producing cells, the AAV vector may be introduced by any suitable method, such as, e.g., by $Ca^{2+}$-, liposome- or protein conjugate-mediated transfection, electroporation or any other method known to those of skill in the art. Using the second method is preferred in certain embodiments as the infectious virus will generally also promote the efficient transfection and subsequent propagation of the AAV vector.

The double and triple infection methods require the use of a second and/or third recombinant virus which is capable of infecting host cells and, therefore, the requirement for DNA transfection is completely removed. Such methods need adenovirus or herpes virus constructs which contain a non-replicative, recombinant AAV vector which will integrate into the host genome but will not be able to direct its own replication or packaging. As with the other AAV vectors, these vectors will generally include AAV inverted terminal repeat sequences along with the expression region encoding the desired protein—which, of course, may be virtually any protein. Although these third and fourth production methods completely overcome the need for transfection, it should be noted that all the methods of the present invention represent a distinct advantage over the prior art as once a cell capable of producing AAV is initially established, recombinant AAV may be generated by repeated infection.

Whichever route is chosen to deliver the AAV vector into a cell to form an AAV-producing cell, the AAV generative process will need only the cells to be functionally contacted, i.e., infected, by the recombinant infective virus described herein. This process of activation, which may also be termed AAV rescue, is the process by which the AAV vector-containing cells are stimulated to produce recombinant AAV virions by supplying them with the remaining AAV functions needed for replication and packaging. This will often require infecting the cells with recombinant adenovirus or herpes virus encoding AAV rep, lip and cap, especially when the recombinant AAV to be generated includes a larger DNA insert.

Using the old transfection methods, only a few percent of cells would receive DNA from both plasmids and produce recombinant AAV virions. Whereas using the new invention, 100% of cells can receive AAV viral genes via infection, e.g., with AdAAV, and release recombinant AAV virions. The average number of transducing AAV produced per cell is also greatly increased. From a practical standpoint, the amount of transducing AAV produced with this new approach is only limited by the cell culture capacity of the manufacturing facility.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

GENERATION OF RECOMBINANT ADENOVIRUS THAT EXPRESS ESSENTIAL PROTEINS FOR AAV PACKAGING

Recombinant adenovirus (AdAAV) can be constructed using recombinant DNA and in vivo homologous recombination technologies. The genomic structure of one particular AdAAV and the strategies for making this recombinant virus are schematically diagrammed in FIG. 2. The strategy for making this recombinant virus may be adapted for the generation of other recombinant adenoviruses.

To construct AdAAV, the rep-cap genes were excised at the Xbal sites from a DNA clone of AAV2 (pSub201, Samulski et al., 1987). The rep-cap fragment contains the left-most promoter, P5, and all of its transcriptional regulatory elements at the 5'-end of the fragment and the common polyadenylation site at the 3' end. This fragment was then inserted into the Xbal site of pXCX2 (FIG. 2) which contains the left 16% of the Ads genome, minus a deletion in E1 from 1.3 to 9.3 map units (Spessor et al., 1989). The resulting plasmid which contains the AAV genes was designated pXCX-AAV.

DNA of pXCX-AAV plasmid was then amplified in DH-5 E. coli and purified by CsCl gradient centrifugation using standard techniques (Sambrook et al., 1989). In 293 cells, the purified pXCX-AAV was then recombined with the right portion of the adenovirus genome (Ad.E3) which is deleted in the E1 and E3 regions. The Ad.E3 DNA was prepared from Ad.E3 adenovirus as described by Graham & Prevec (1991).

Homologous recombination of pXCX-AAV and Ad.E3 in vivo was achieved by co-transfection of pXCX-AAV and AdE.3 DNA into 293 cells using a standard $CaPO_4$ transfection method (Sambrook et al., 1989). Each of 100 mm-plate of 293 cells at 70 to 80% confluence were co-transfected with a mixture of 20 µg DNA containing equal amount of pXCX-AAV and Ad.E3 DNA. The Ad.E3 DNA had been digested with Xbal and Cla1 restrictions enzymes prior to transfection to increase the chance of recombination. At 18 hr post transfection, cells were overlayed with 0.5% low melting point agarose (ultra Pure LMP Agarose, BRL) in DMEM containing 10% horse serum. Cells were then incubated in a $CO_2$ incubator for 10 days, and fed with DMEM containing 10% of horse serum every 3 days, layered on top of the agarose.

On day 10, visible plaques of adenovirus infected cells were picked and re-inoculated into individual wells of 24 well plates containing 293 cells that had been freshly seeded the night before. Most of the cells showed cytopathic effect (CPE) between 3 and 5 days after inoculation. These cells were harvested and lysed in 1 ml of DMEM using light sonication. Each viral sample was divided into two portions of 0.5 ml each. One was used to infect 293 cells in a 100 mm-plate while the other was stored at −85° C. as a backup stock. Viral DNA from the recombinant adenovirus was isolated from each of the 100 mm plate as described by Graham & Prevec (1991) when about 90% of the cells in each plate showed CPE.

Figure 4A:
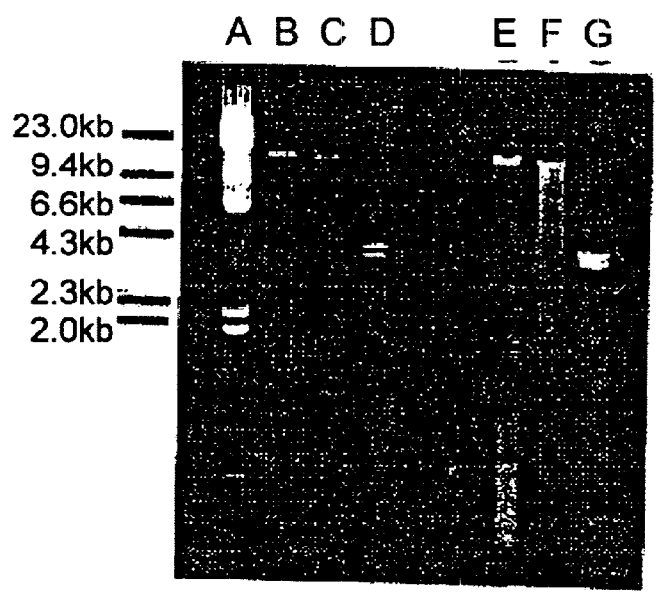
FIG. 4A. Agarose gel, lane A is DNA standard of lambda/Hind III fragments; lanes B, C and D are AdΔE3, AdrcE1 and SSV9 DNA, respectively, digested with XbaI restriction enzyme; lanes E, F, and G are 4 times greater amounts of each of same DNA samples as in lanes B, C and D. In lanes C and F, an Xba-fragment can be seen in a same size as that of rep-lip-cap fragment (4.4 kb) from SSV9 generated by XbaI digestion. While in the parental virus, AdΔE3, this 4.4 kb fragment is absent.
Figure 4B:
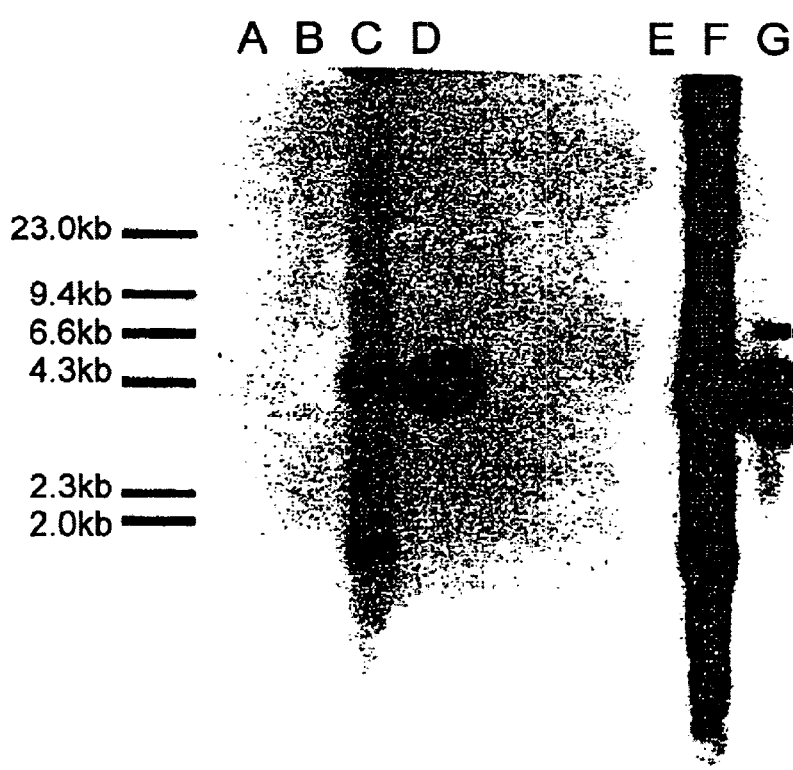
FIG. 4B. Autoradiograph of the agarose gel described in FIG. 4A. The 4.4 kb fragments in both Lane C and F are strongly hybridized to the rep-, cap-specific DNA probes, as well as the 4.4 kb fragments in Lane D and G which are positive controls. In contrast, none of the DNA in the AdΔE3 and the lambda/Hind III-DNA standard hybridized to the probe.

The correct recombinant adenovirus, AdAAV1 (FIG. 3), was identified by restriction enzyme mapping of the viral genome using Xbal digestion and hybridization with a radioisotope labeled DNA probe specific for the AAV sequence on a Southern blot assay (Sambrook et al., 1989), as shown in FIG. 4. AdAAV1 was then propagated to a high titre in 293 cells and aliquoted for storage and subsequent analysis.

EXAMPLE II

GENERATION OF REPLICATION-COMPETENT RECOMBINANT ADENOVIRUS THAT CONTAIN AAV REP-LIP-CAP IN THE E3 REGION

This example concerns the generation of a replication competent adenovirus that contains the rep-lip-cap genes of AAV inserted into regions other than the E1 region and, particularly, into the E3 region. This is advantageous as the level of E1 protein expression, and consequent recombinant AAV production, in cell lines such 293 cells is lower than that in cells infected with E1-containing adenovirus. The recombinant virus described in this example may also be advantageously used in double infection techniques (see Example VIII) for AAV production where the recombinant adenovirus that provides AAV genes and the recombinant adenovirus that carries the AAV vector complement each other for the replication defect.

To make a replication competent adenovirus that contains the rep-lip-cap genes of AAV, plasmid pSub201 is digested with Xbal restriction enzyme. The 4.4 kb AAV fragments is isolated and ligated with pFGdX1 which also has been digested with Xbal enzyme. Ligated DNA is then trans formed into competent E. coli. Correct pFGrc, which contains the rep-lip-cap DNA fragment in the same orientation as that of E3 is identified by enzymatic digestion of plasmid DNA.

The replication-competent recombinant adenovirus which contains rep-lip-cap genes is generated by in vivo homologous recombination of pFGrc and adenoviral DNA isolated from Adenovirus 5 in the same manner as described hereinabove. The resulting recombinant adenovirus is named Adrc3.

In inserting the rep-lip-cap genes of AAV into the E3 region of an adenovirus, the 4.4 kb AAV insert means that the recombinant adenovirus reaches the maximal packaging capacity. This will reduce the frequency of generating recombinant adenovirus. The packaging efficiency of such recombinant adenovirus also will be reduced, therefore the titer of infectious particle will be lower than that of wild-type adenovirus. To overcome this, a small region between the E4 and the end of the genome can also be deleted. Alternatively, part or the entire of the E4 region can be deleted. The in vivo homologous recombination will be achieved using E4 complementing cells in a similar way as that of E1 complementing cells discussed herein. Because E4 is essential for adenovirus replication, a recombinant adenovirus lac of E4 has to be used in combination with an adenovirus that contains an intact E4 region, such as AdAV-lacE1.

EXAMPLE III

GENERATION OF REPLICATION-COMPETENT RECOMBINANT ADENOVIRUS THAT CARRY REP-LIP OR CAP GENES SEPARATELY

The present example addresses two aspects of the invention, namely the generation of further replication competent adenoviruses and the generation of adenovirus which carry separate rep-lip or cap genes. Again, these recombinant DNA and in vivo homologous recombination methods may be adapted to prepare any particular recombinant virus desired.

The rep-lip-cap genes of AAV can be inserted into two separate recombinant adenoviruses. In this particular arrangement, rep-lip or cap gene can be inserted in the place of the E3 region without the need to make other deletions in the adenoviral vector. Since the E3 region is not essential when the viruses are propagated in cell culture, these recombinant adenoviruses (Adrep3 and Adcap3) are replication-competent. This eliminates the need for special cell lines that complement the essential genes deleted from the adenoviruses, such as 293 cells to complement E1 region, or the need of mixing wild type adenovirus to provide the deleted gene in trans.

Figure 5:
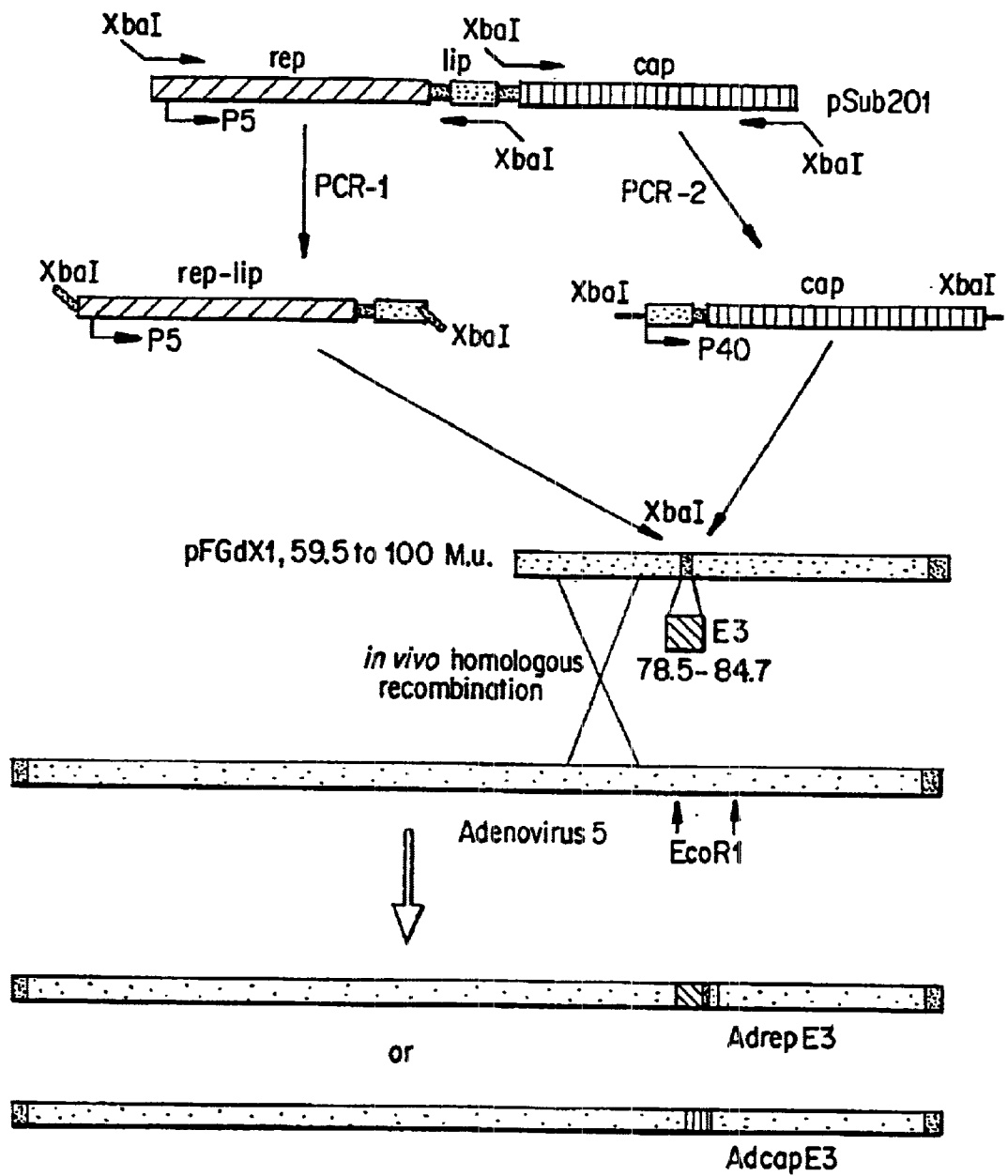
FIG. 5. A schematic diagram of the strategy for separately inserting AAV rep-lip and cap genes into the E3 region of adenoviruses. The AAV2 genome, pSub201, is diagrammed at the top of the drawing. The rep, lip and cap genes are represented by patterned boxes. A pair of light gray arrows represents the PCR primers which were used to amplify the rep-lip genes. A pair of dark gray arrows represents the PCR primers used for cap gene amplification. The PCR products of rep, lip or cap genes, were inserted into the E3 region of pFGdX1 construct, respectively. The rep, lip or cap genes were then inserted into the E3 region of adenovirus 5 genome (represented by gray box) by in vivo homologous recombination.

To insert rep-lip in to the E3 region, the rep-lip gene including the P5 promotor (promotor 1) is amplified using PCR (polymerase chain reaction) techniques using a pair of primers which contain Xbal sites, as diagramed in FIG. 5. The cap gene is also PCR amplified in a similar way with specific primers (FIG. 5). The two gene fragments, rep-lip and cap, are then digested with Xbal enzyme and inserted into the unique Xbal site of pFGdX1, respectively. The FGdX1 plasmid contains the right-hand portion of adenovirus 5, from map unit 59.5 to 100, which also has a deletion from map unit 78.5 to 84.7 (E3 region).

It is important to insert the cap gene in the same direction as that of E3 region so the cap gene can be transcribed from the E3 promotor. The cap gene also can be amplified with the promotor 3 to drive the cap gene expression. Alternatively a heterologous promotor, such as CMV early promotor or the P5 promotor (promotor 1), can be inserted up-stream of the cap gene to boost the expression. In any case, it is preferred to insert rep-lip or cap gene in the same orientation as that of E3 to avoid the interference of the transcriptional product from E3 promotor (potential anti-sense RNA). In this case, the pFGdX1 plasmids containing the rep-lip or cap genes are named pFGrepE3 and pFGcapE3, respectively.

Recombinant adenoviruses carrying the rep-lip or cap gene are generated by in vivo homologous recombination of pFGrep or pFGcap with purified adenovirus DNA which has been digested with EcoR1 restriction enzyme. The detailed procedure is essentially the same as that described hereinabove and by Graham Prevec (1991). Plaques of recombinant adenovirus, Adrep3 and Adcap3, will be purified and propagated as described hereinabove in Example I.

EXAMPLE IV

GENERATION OF RECOMBINANT ADENOVIRUS THAT CONTAIN AN AAV VECTOR

The present example describes methods the generation of recombinant adenovirus that contains an AAV vector, the strategy for which is essentially the same as that for generating a recombinant adenoviruses that express AAV proteins, as described above.

To insert an AAV vector into adenovirus, plasmid pXCX2 was digested with Xbal restriction enzyme and blunt-ended by Klenow enzyme treatment following the protocol described by Sambrook et al., (1989). An AAV viral sequence was excised from pSub201 using the two PvuII restriction sites which flank the two ITR sequences. This AAV fragment is ligated into the pXCX2 vector. The resulting plasmid was named pXAV. The AAV genes (rep, lip, and cap) were then removed from the vector using the two SnaBI sites and replaced with a lac-Z gene within a CMV immediate-early transcription unit. This construct was designated as pXAVlac. The plasmid, pXAVlac, was then used for in vivo homologous recombination to generate the recombinant adenovirus.

The above cloning procedure was used because the Pvu II sites were presented in the lacZ gene which make it necessary to insert the ITR sequence of AAV and the gene of interest, in this case the lacZ gene, in a step wise fashion. Naturally, the detailed cloning procedure may vary depending upon the gene of interest to be inserted.

Different plasmids other than pXCX2 also can be used depending on the region in which the AAV vector is to be inserted. For example, the AAV vector can be inserted into the E3 region. In this case the plasmid, pFGdX1 (Haj-Ahmad & Graham, 1986), or an equivalent can be used. The FGdX1 plasmid contains the right side portion of adenovirus 5, from map unit 59.5 to 100, which also has a deletion from map unit 78.5 to 84.7 (E3 region). An AAV vector can be inserted into pFGdX1 at the unique Xbal site, where E3 region is deleted.

The generation of recombinant adenoviruses which contain an AAV vector was performed in the same way as that described above for AdrcE1. The resulting recombinant adenovirus was named as AdAVlacE1.

EXAMPLE V

PROPAGATION OF RECOMBINANT ADENOVIRUS, AdAAV

To propagate AdAAV, 293 cells (from ATCC) were washed twice with serum-free medium (DMEM, Delbecco's) and infected with AdAAV at a MOI of 5–10. After a majority of the cells exhibited CPE (cytopathic effect), the cells were harvested by scraping and lysed by sonication or multiple freeze-thaw cycles. Cell debris were removed by low speed centrifugation (2000 rpm for 20 min.) The supernatant can be frozen for storage or used directly to infect producer cells for AAV production. Purified virus can also be prepared using CsCl gradient centrifugation according to Graham and Prevec (1991).

EXAMPLE VI

GENERATION AND PROPAGATION OF RECOMBINANT HERPES FAMILY VIRUSES THAT EXPRESS ESSENTIAL PROTEINS FOR AAV PACKAGING

In addition to recombinant adenovirus (AdAAV), viruses of the herpes class may be engineered to express essential AAV genes and employed in recombinant AAV production. In particular, herpes simplex virus (HSV), cytomegalovirus (CMV), pseudorabies virus (PRV) and Epstein-Barr Virus (EBV) may be employed (Bauer & Monreal, 1988; Buller & Rose, 1978; Hogan et al., 1972; McPherson & Rosenthal, 1985; Parks et al., 1967, Meignier et al., 1987; Keller et al., 1986).

HSV, CMV, PRV and EBV are particularly suitable for engineering to express essential AAV genes as they all have a large DNA genome which contains regions that are not essential for replication, at least in vitro, or regions that can be deleted and complemented in trans. Accordingly, the rep-lip-cap genes of AAV can be inserted into the genome of these helper viruses using essentially the same the in vivo homologous recombination and propagation strategy described above for recombinant adenovirus and modified as follows.

1. Recombinant HSV Expressing Essential AAV Genes

Like the recombinant adenovirus, herpes viruses which contain suitable deletions are not naturally available and they have to be engineered by artificial deletion, e.g., using techniques similar to that for making deletions in adenovirus (Post & Roizman, 1981; Meignier, et al. 1987). One such HSV vector, R7020, was constructed from HSV-1 (F) using several steps of recombination and deletions (Meignier, et al. 1987). The recombinant HSV lacks approximately 700 bp from the domain of the thymidine kinase (tk) gene and all of the sequences from the 3' end of the $\alpha 27$ gene situated near the right terminus of unique sequences of the L component to the promoter regulatory domain of the $\alpha 4$ gene in the reiterated sequence of the S component. In place of the internal inverted repeat sequences, a DNA fragment cloned to form the HSV-2 genome and encoding the viral glycoproteins G, D, and I, and the tk gene driven by the $\alpha 4$ gene promoter.

In R7020, or a similar recombinant, the rep-lip-cap genes of AAV can be inserted in, at least, either of the two positions. These sites are between the inserted tk gene and the HSV-2 DNA sequences and the site of the deletion in the natural tk gene. The total capacity of R7020 virus for additional DNA sequences exceeds 10 kb. Therefore it is also possible to insert an AAV vector that carries a gene of interest into the same HSV vector at a different position from that of the essential AAV genes. The detailed techniques for inserting AAV genes into HSV are the essentially the same as the standard methods described by Mocarski et al., (1980) and Post & Roizman (1981), each incorporated herein by reference.

2. Recombinant Pseudorabies Virus Expressing AAV Genes

PRV is an alphaherpesvirus of swine. PRV has a very broad host range, but does not infect humans. Like the adenovirus, PRV also can be manipulated easily by recombinant DNA techniques to express genes of interest. As with HSV described above, there are a number of nonessential locations of the PRV genome where foreign DNA can be inserted in a PRV vector. One such region is the tk gene. Other nonessential regions include glycoprotein gIII gene (Keeler, 1986), gX glycoprotein gene and much of the short unique ($U_S$) portion of the PRV genome.

While all of the above nonessential regions can be used for inserting AAV genes, it is preferable to insert genes such as rep-lip-cap genes into the position of tk gene of PRV. This is because the recombinant PRV, in which the AAV genes have replaced the tk gene, becomes iododeoxyuridine resistant. The recombinant virus can then be selected with medium containing iododeoxyuridine. For AAV gene expression, the natural AAV gene promoters are included in the insert. Therefore the transcription from the PRV tk promoter is not essential. When the tk promoter is kept in the vector, the AAV gene should be inserted in the same orientation as that of tk gene to prevent transcriptional interference from the tk promoter. For propagating recombinant PRV, VERO cells (an african green monkey kidney cell line) may be advantageously used.

3. Recombinant Cytomegalovirus to Express AAV genes

Cytomegaloviruses are very large DNA viruses with approximately 240 kb DNA genomes which encode over 100 gene products in three kinetic classes, referred to as immediate early ($\alpha$), delayed early ($\beta$), and late ($\gamma$). Several regions of the huge genome of CMV have been found nonessential for CMV replication, and can be used for the insertion of foreign genes such as essential AAV genes.

The two most commonly used regions for foreign gene insertion are in the major $\alpha$-promotor and $\beta^{2.7}$ promoter transcriptional regions. Again, the basic in vivo homologous recombination techniques described in the earlier examples may be used, and in this case, supplemented if necessary by references such as that of Mocarski et al., (1980). Recombinant CMV expressing essential AAV genes can be propagated in NIH-3T3 cells or in any cell type that is susceptible to CMV infection.

EXAMPLE VII

ESTABLISHING AAV-PRODUCING CELLS

AAV-producing cells are cells which contain an AAV vector carrying the gene of interest which can be rescued when supplied with the required essential AAV genes. In certain embodiments, AAV-producing cells will, themselves, complement the replication-defective nature of the adeno- or herpes virus vector which is to be used. One example is 293 cells which express the E1 protein and which contain an AAV vector bearing the gene of interest. Several methods are suitable for generating AAV-producing cells, such as those described below, and any method may be employed.

Method 1: Simultaneous AAV Transfection and AdAAV Infection

Transfection and infection may be performed at the same time, with a single procedure. In this procedure, AdAAV is added into the transfection mixture during transfection (MOI at 20–100). Any of the standard known transfection procedures may be employed (Sambrook et al., 1989), e.g. liposome or protein conjugate transfection procedures. Then recombinant adenovirus, AdAAV, serves two purposes.

First, it provides all the proteins essential for AAV replication and packaging. Second, it also greatly enhances the efficiency of transfection by the facilitating the escape of vector DNA from the lysosome.

Three days post-transfection, the cells were lysed by freeze-thaw or sonication, and centrifuged at low speed to remove cell debris. The supernatant was then heated at 56° C. for 10 min. to inactivate the majority, but not all, of the AdAAV that were released together with the recombinant AAV. This is necessary to increase the AAV/Adenovirus ratio of the viral stock. This stock was then used to infect fresh 293 cells to further propagate the AAV virions. When most 293 cells show CPE, cells were harvested and lysed as described above. This procedure of propagating virus can be repeated more than once to enhance the concentrations of recombinant AAV produced.

After the last propagation, the viral stock was heated at 56° C. for 30 min. This longer heat treatment completely inactivated the AdAAV. The recombinant AAV stock can be purified and concentrated or used directly to infect 293 cells at the highest possible MOI. Since the AAV genome will stably integrate into the cell's chromosomes in the absence of adenovirus, the progeny of these transduced cells will also have multiple copies of AAV vectors in their chromosomes. Therefore, the transduced cells can be multiplied in cell culture to large numbers. These cells can be aliquoted and stored using standard techniques. When the cells are infected with AdAAV, the AAV vectors that are integrated in the producer cells will be activated and replicated, and they will be packaged into AAV virions.

Method 2: Prior Transduction with AAV Virions

An alternative approach is to use existing procedures to make small amounts of recombinant AAV (Muzyczka, 1992), and to transduce 293 cells with these AAV virions. The transduced cells then become producer cells. The producer cells will release recombinant AAV when infected with the AdAAV, which provides all the proteins for viral production.

In this method, an AAV vector that contains a gene of interest is co-transfected with a helper plasmid that expresses AAV genes (rep and cap) into adenovirus infected cells (MOI of 1–5). Three days post-transfection, the cells are lysed and subjected to a low speed centrifugation to remove cell debris. The supernatant is heated at 56° C. for 30 min. to inactivate the adenovirus, and then used to infect 293 cells without dilution in order to achieve the highest possible MOI. For this procedure, it is preferable to use AAV virions purified by CsCl gradient centrifugation. This will insure that most, if not all, of the 293 cells are infected with the recombinant AAV that contains the gene of interest.

When establishing producer cell lines, it is important to transduce 293 cells at the highest possible MOI to insure that most of the cells contain integrated AAV vectors. If the gene of interest is smaller than 3.5 kb, a small selection gene, such as the bleomycin, puromycin or neomycin resistance genes, can also be inserted into the vector. In this way, the producer cells can be selected with the appropriate antibiotics to yield a higher homogeneity. For large scale production of transducing virions, suspension cultures of the AAV-producing cell lines may be established using suspendable 293 cells, 293N3S (Graham & Prevec 1991).

EXAMPLE VIII

PRODUCTION OF TRANSDUCING AAV VIRIONS

Once the AAV producing cells and/or recombinant adenoviruses are generated, the production of recombinant AAV rely solely on infection. Several different procedures can be applied to produce recombinant AAV, as exemplified in this section.

1. Producer Cell Lines

Producer cells can be cultured in large amounts, depending on the scale of production required. Producer cells are then infected at a MOI of 5 to 20 with a mixture of adenovirus, containing 70–90% of recombinant adenovirus expressing AAV genes and 10–30% of an adenovirus which has an intact E1 region. Three to four days post infection, the cells are harvested and lysed by sonication. After removal of the cell debris by low speed centrifugation, the recombinant AAV can be purified by one or a combination of several techniques, such as by saturation of the supernatant with CsCl and banding in a CsCl gradient generated by ultracentrifugation, by heat in activation of adenovirus, or by chromatography.

Figure 6A:
FIG. 6A. Cells infected with recombinant AAV. The majority of the cells turned blue after staining.
Figure 6B:
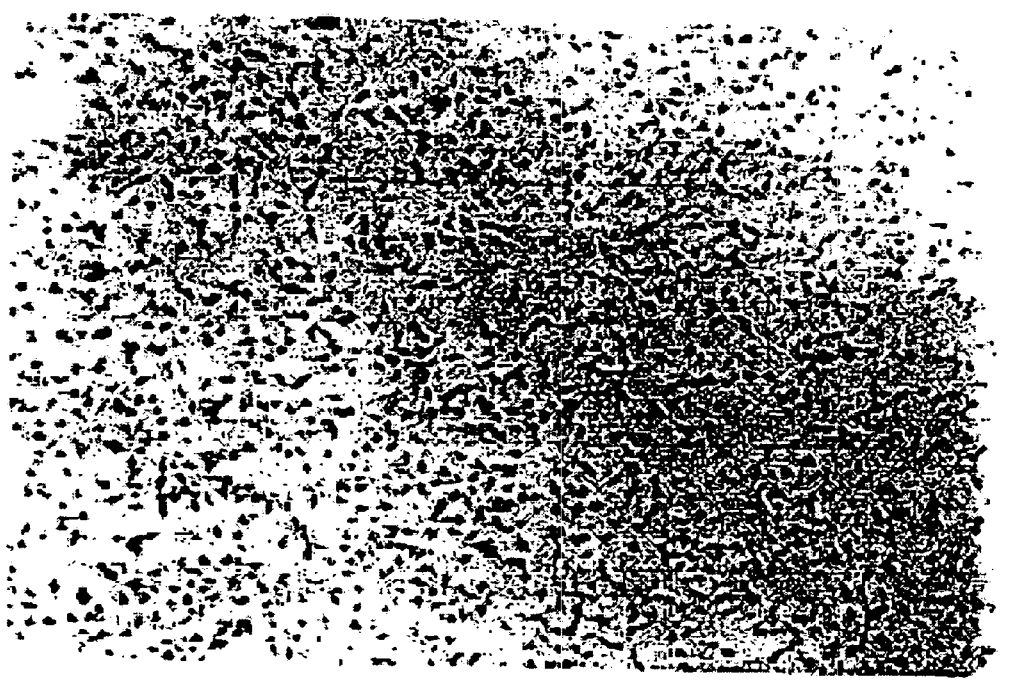
FIG. 6B. Uninfected HeLa cells stained in the same way as the infected cells, no blue cells can be observed.

The results of one example of AAV production using producer cell lines and recombinant adenovirus that carry the AAV genes is shown in FIG. 6. In this specific example, an AdrcE1 virus was used to infect producer cells bearing an AAV-lacZ vector, which resulted in the generation of recombinant AAV virions carrying lacZ genes. 293 cells were transfected twice with an AAV vector containing a LacZ gene in a CMV transcription unit (pAVcmvlac) using Lipotransfectamine (Gipco & BRL) and infected with the AdAAV termed AdrcE1 and 10% of wild type Ad5. Three days post transfection, the cells were lysed and sonicated for 10 seconds. After removal of the cell debris by low speed centrifugation, the supernatant was used to infect HeLa cells. At 24 hours post transfection, the cells were fixed with 0.3% glyceraldehyde, stained with X-Gal and photographed under an inverted light microscope. It can be seen that the majority of the cells infected with recombinant AAV turned blue after staining (FIG. 6A), whilst no blue cells were observed in the uninfected HeLa cells stained in the same way (FIG. 6B).

It should be noted that, in addition to the details described hereinabove, U.S. Pat. No. 5,173,414, incorporated herein by reference, describes suitable methods for harvesting AAV virus. To harvest virus in the manner of U.S. Pat. No. 5,173,414, cells and medium may be collected and the cells completely lysed by two 1-sec pulses of sonication. The virus (i.e., viral stock) may then be cleared of cellular debris by centrifugation. Wild-type adenovirus may be inactivated by heating the stock at 56° C. for 30 minutes. Before use, the stock may be filtered through a 1 micron, or preferably, through a 0.45 or even 0.2 micron, cellulose acetate membrane.

2. Infection Procedures

Another approach for creating large quantities of AAV involves a double, or even triple, infection process. This does not, technically, involve preparing a producer cell line, but does require the creation of a second recombinant adenovirus. This method is more efficient once the second recombinant adenovirus has been generated. Several double and triple infection methods for producing recombinant AAV are available, depending on the combinations of recombinant adenoviruses employed. The creation of additional recombinant adenoviruses that carry an AAV vector containing a gene of interest is disclosed herein, e.g., see Example IV. The strategy for double infection is diagrammed in FIG. 7.

For example, in one approach, an AAV vector containing the gene of interest is inserted into a recombinant adenovirus in the same way as the AdrcE1. This eliminates the requirement for a producer cell line. High titers of recombinant AAV are generated by co-infecting 293 cells with AdrcE1 and the recombinant adenovirus that carries the AAV vector and a therapeutic gene. If both recombinant adenovirus carry the inserted AAV genes and AAV vectors in the E1 regions, such as AdrcE1 and AdAVlacE1, it is recommended to mix 10–30% of adenoviruses that have an intact E1 region into these recombinant adenoviruses before co-infecting 293 cells. The E1 containing adenovirus, such as wild-type adenovirus, will provide additional E1 proteins in the infected cells. This boosted level of E1 protein is required for efficient AAV protein synthesis and AAV vector replication.

The most favorable combination is that AAV genes and AAV vector are inserted at different regions of the recombinant adenoviruses, such as AdAVlacE1 and AdrcE4 (in which the rep-lip-cap genes are inserted at E4 region). Therefore, when the two adenoviruses are used to co-infect cells, their defect will be complemented by each other. AdAVlacE1 also can be used in combination with replication competent recombinant adenovirus such as the combination of AdAVlacE1 and AdrepE3/AdcapE3 or AdAVlacE1 and Adrc3. In these cases, the E1 proteins are produced by the E1 containing adenovirus, AdrepE3, AdcapE3 or Adrc3, and the production of recombinant AAV can be done in any cells that are susceptible to adenovirus infection, such as BK or HeLa cells.

3. Double Infection Combination of AdrcE1 and AdAVlacE3.4

In adenovirus, AdrcE1, the rep-lip-cap genes of AAV are inserted into the E1 region adenovirus while in AdAVlacE3.4, the AAV vector containing the lac-Z marker gene is inserted into the E3 region, and part of the E4 region is also deleted to make enough packaging space for the insertion of AAV vector. In this combination, any cells that are susceptible to adenovirus infection can be used for recombinant AAV production. This is because the E1 defect of AdreE1 can be complemented by the AdAVlacE3.4. The E4 defect of AdAVlacE3.4 is complemented by AdrcE1.

A similar complementation can be achieved by insert the AAV vector into the E1 region (AdAVlacE1) and the rep-lip-cap genes into E3 or E4 region (AdrcE3.4).

4. Double Infection Combination of AdrcE3 and AdAVlacE1

Recombinant adenovirus, AdrcE3, contains the rep-lip-cap genes of AAV in its E3 region. AdrcE3 is replication competent since the E3 region is not essential for adenovirus which carry an AAV vector, such as AdAVlacE1, AdAVlacE2, AdAVlacE4, as well as adenoviruses that contains deletions in the late genes. When AdrcE3 is used, any cells that are susceptible to adenovirus infection can be used without the need to provide E1 proteins in the cell line or by wild-type adenovirus infection. AdrcE3 also can be used to infect AAV vector producing cell lines, and the producer cell line can be made with any cells that are susceptible to adenovirus infection.

5. Triple Infection Combination: AdAVlacE1 and AdrepE3/AdcapE3

When this three-recombinant adenovirus system is used the rep-lip and cap genes are carried separately by two adenoviruses in their E3 regions, and the AAV vector is carried by a third adenovirus in the E1 region. When cells are infected with all three of these adenoviruses, recombinant AAV that carry the gene of interest will be produced along with the recombinant adenoviruses. The E1 defect of AdAVlacE1 is complemented by both of the AdrepE3 and AdcapE3. Both AdrepE3 and AdcapE3 are replication-competent in cell culture since the E3 region is not essential for replication.

The critical components of the systems described in the first eight examples are a recombinant adenovirus or herpes virus that expresses the AAV rep and cap proteins, and either producer cell lines or other infectious virus for use in double infection. The major difference between this system and previous ones are, firstly, that the AAV vector is integrated into the producer cells or inserted into a recombinant adenovirus which can be propagated in large amounts. Secondly, once an AAV-producing cell line is established, recombinant AAV virion production requires only infection with AdrcE1 or an equivalent recombinant virus, which is a very efficient procedure. When a Double Infection procedure is used both AAV genes and therapeutic AAV vector are carried by adenovirus and the production of recombinant AAV only requires infection and can be done in any cells susceptible to adenovirus infection. The detailed procedure for manufacturing recombinant AAV virions can be varied and optimized to meet the demands of specific procedures and/or scales of production.

EXAMPLE IX

CONSTRUCTION OF FURTHER AAV VECTORS

This example concerns the creation of further specific AAV vectors which may be employed in the pre-clinical planning of gene therapy, for example, as may ultimately be used in the treatment of cystic fibrosis.

1. Construction of a Minimum-Sized AAV Vector that Contains the CFTR Gene

Wild type AAV contains a single-stranded genome of 4575 nucleotides. It is generally believed that the virus can package a genome slightly larger than the size of its wild-type genome, although with a reduced efficiency. The maximum packaging capacity of AAV is suggested to be about 5000 nucleotides (Muzyczka, 1992). To achieve efficient packaging of AAV vectors containing the CFTR gene, a series of truncated forms of the CFTR gene have been expressed from an AAV based vector (Egan et al., 1992). However, a truncated CFTR is far from ideal as a choice for functionally replacing the wild-type CFTR in gene therapy.

To efficiently transduce a full length CFTR gene from an AAV vector it is necessary to further reduce the size of the AAV vector. It has been shown that the left end 145 nucleotides and the right end from the common polyadenylation site to the end of the 145 nucleotide repeat is sufficient for genome replication, packaging and viral integration (Muzyczka, 1992). Recently it was reported that the 145 bp repeat also contains promoter activity from which a CFTR gene can be expressed (Flotte et al., 1992). The polyadenylation site is about 100 bp upstream of the right-hand ITR. This makes it possible to create a minimal sized AAV vector of 400 bp (FIG. 8), which can carry an inserted gene of 4.5 kb, the length of the CFTR coding sequence.

Figure 8:
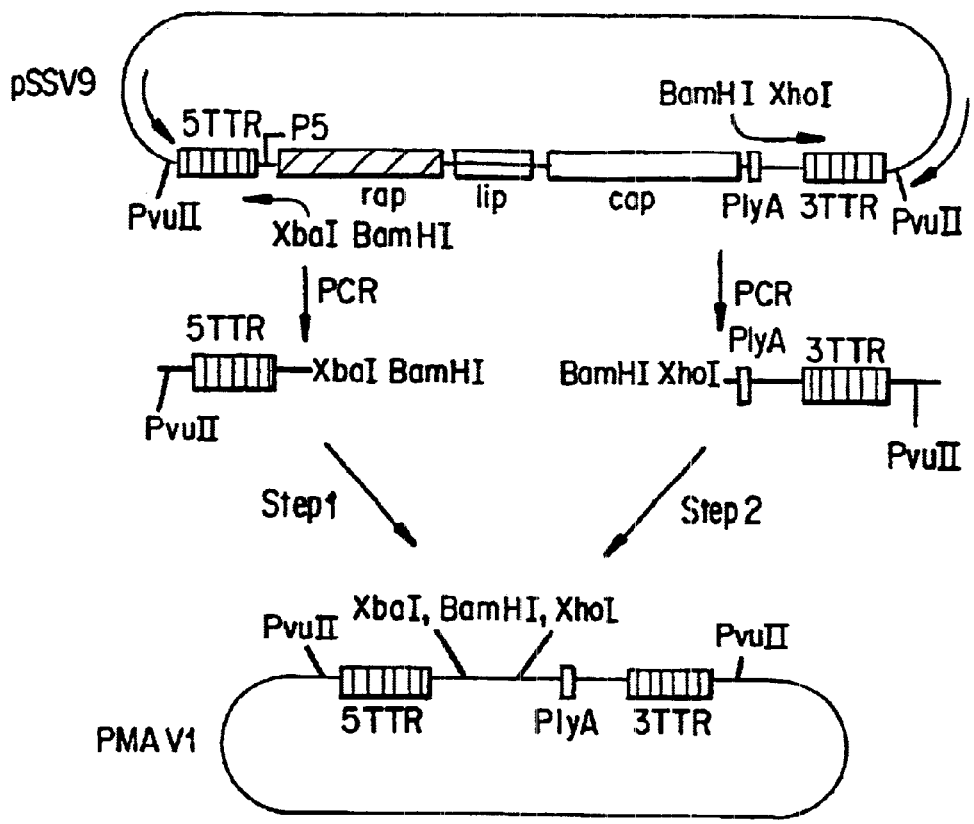
FIG. 8. A schematic diagram of the cloning of the mini-AAV vector. Boxes represent reading frames of viral genes. Two paris of gray arrows indicate the locations of primers used for PCR. ITRs, polyadenylation site and restriction sits are labeled individually.
Figure 9:
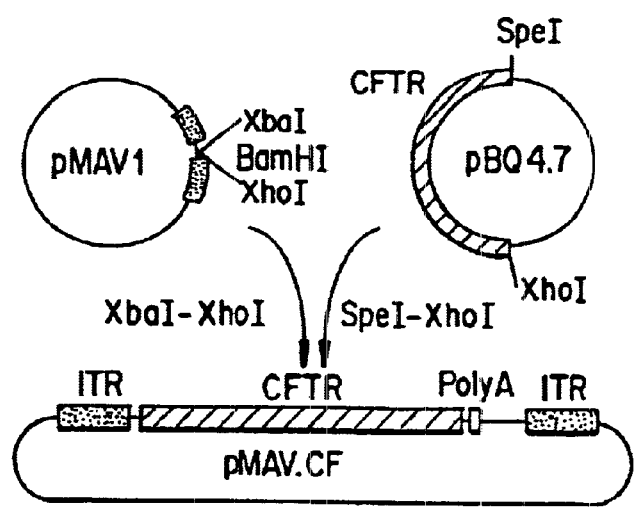
FIG. 9. Schematic diagram of expression of a full length CFTR gene from AAV vector. CFTR gene form pBQ4.7 was inserted into pMAV1 using the two cloning sites. CFTR gene is represented as hatched box and ITRs are represented as black box.

A plasmid that contains an infectious AAV clone (pSSV9) was used for the construction of a minimum-sized vector (FIG. 8). The AAV genome was flanked by a pair of Pvu II sites. To delete the entire coding sequence for viral genes (rep, lip and cap) and create convenient restriction sites for CFTR cloning, the left and right end ITR was PCR-amplified with two pairs of primers, as diagrammed in PMAV1 of FIG. 8. The amplified right end and the left end ITR fragments were then cloned back into the pEMBL vector stepwise to replace the entire AAV genome as diagrammed in FIG. 8. The resulting AAV vector contains the left end 145 base pair ITR, a multiple cloning site, a poly adenylation site and the right-end ITR (PMAV1, FIG. 8). The CFTR gene and two of its natural mutants (Δ508 and G551D) were then excised from pBQ4.7 vector with Spe I and Xho I and cloned into the pMAV vector using the two convenient XbaI and XhoI sites (FIG. 9).

2. Construction of Minimum-Sized AAV Vectors Containing Marker Genes

For analyzing the mini-AAV vector, the inventors inserted three different marker genes, chloramphenicol acetyltransferase (CAT) gene, lac-Z gene and neo$^r$ gene into the pMAV vector. For comparing the transcription activity of the ITR with that of a foreign promoter, the SV40 early promoter, three CAT gene containing AAV vectors have been constructed. In one, a CAT coding region including most of the plasmid sequence from pCAT-basic (Promega) was inserted into the Xba I and Sal I site. The insert is 4358 bp in length which is slightly under the size of the CFTR gene. In another, a CAT gene driven by a early SV40 promoter and enhancer from pCAT-control (Promega) was inserted into the pMAV vector. In yet another, the CAT gene is driven by the SV40 promoter only. In a final one, only the SV40 enhancer is present, which will allow the inventors to determine whether the transcriptional activity of the ITR can be enhanced by the SV40 element. Comparing the CAT activity transduced with pMAV-CAT and pMAVsvCAT will enable the relative transcriptional activity of the left end ITR of AAV to be determined.

Vectors to assess the packaging limit may also be designed and employed in connection with the present invention.

3. Development of Advanced AAV Vectors that Express the CFTR Gene Constitutively at Different Levels Independent of the Activation of Adenovirus E1 Protein The expression of AAV viral protein requires activation by adenovirus coded protein and AV1 RNA. The transcription of the AAV promoters are suppressed by a cellular regulatory protein which can be released by the binding of adenovirus E1a protein. Complete deletion of the regulatory sequences (including YY-1 binding site) and the left most promoter (p-5) results in constitutive expression of the gene of interest in the AAV genome. This is presumably because the terminal repeats contain an untypical promoter that can initiate transcription at a low level. Sequence analysis of the 3'-end repeat did not show potential transcription initiation sites which is similar to known promoters within the terminal repeat. Preliminary results from the present inventors show that when β-glycosidase was expressed from the ITR the level of expression was very low, while Neo$^r$ gene expressed from an inserted SV40 promoter confers G418 resistance in cells with a high efficiency.

The full length CFTR gene has been inserted into minimal sized AAV vectors, however, the size of the vector is slightly larger than the optimal packaging size of AAV. In addition, the low level of transcriptional activity of the ITR from which the CFTR gene is expressed make these vectors sub-optimal for gene therapy. To increase the efficiency of transcription and minimize the size of the vector for packaging efficiency, new vectors will be created to contain a minimum-sized synthetic promoter without the regulatory sequences. Thus the inserted gene will be constitutively expressed at a higher level, independent of the activation by adenovirus coded proteins.

In the second set of vectors, the translation enhance sequence Kozak motif (MK) will also be created downstream of the synthetic promoter to enhance translational activity and keep the 5'-untranslated region at a minimal length. In this set of vectors, the level of gene expression will be controlled by the promoter sequence at the transcriptional level, and the Marylin Kozak sequence at the translational level.

The new vectors will contain the left and the right end 145 nt ITRs. The synthetic promoter will be inserted immediately downstream of the left-end ITR. The length of the synthetic promoter will be kept at less than 100 bp. This increase in the vector size will be compensated by further deletion of the sequence between the common polyadenylation site for AAV mRNAs and the right-end 145 bp ITR. Since both the positive and the negative strand genome of AAV can be packaged at a equal efficiency, it is unlikely that the packaging sequence lies within the sequence between the polyadenylation site and the right end ITR, because this would require the packaging sequence to function in either polarity of the strand and at either end of the genome. It is possible that this extra sequence, about 100 nucleotide long, can also be deleted from the AAV genome to further shorten the essential sequences of the vector. Therefore a minimal sized AAV vector with the synthetic promoter can be kept under 400 bp, which can carry an inserted gene of 4.5 kb, the size of a CFTR coding sequence. To make sure that the deleted sequence does not contain any sequences that may be required for genome packaging, the transduction rate of the vectors with and without the extra sequence will be compared using a CAT gene construct.

EXAMPLE X

AAV-MEDIATED GENE THERAPY FOR CYSTIC FIBROSIS

This example concerns the development of the use of AAV vectors in gene therapy for cystic fibrosis, and represents just one way that AAV produced by the methods of the invention may be employed.

AN AAV based vector that can effectively package the CFTR gene into virions and constitutively express CFTR gene in targeted cells has been developed. To overcome the limitation of packaging size, a minimum-sized AAV vector containing synthetic transcription and translation initiation sequences was developed in order to increase the packaging efficiency and to express the CFTR gene independent of the presence of adenovirus.

To evaluate the efficacy of gene therapy for CF in the CF mouse model, the CFTR gene will be introduced into the intestine of CF mice using the AAV-CFTR vector to evaluate the therapeutic effect of the CFTR gene. The intestinal pathology of the CF mice transduced with wild-type CF gene will be analyzed in comparison with that of untransduced knock-out CF mice. This will provide direct evidence for the efficacy of gene therapy of CF.

Next, a protocol for the in vivo transfer of the CFTR gene into lungs of animals models will be developed and optimized. Methods of delivering the transducing particles will be tested and optimized for a practical protocol for gene therapy in vivo. Lastly in the pre-clinical stage, the stability of transduced genes in quiescent epithelial cells and animal models will be determined. The duration of expression of the integrated gene transduced with the AAV vector will be studied using reporter genes in primary epithelial cells and animal models.

The following sections set forth various compositions and methods which are envisioned to be of use in just a single treatment method in which recombinant AAV of the invention may ultimately be employed.

1. Functional Analysis and Immunofluorescent Staining of CFTR

The inventors have the ability to monitor CFTR expression using functional assays and immunocytochemistry. This has already been achieved using pancreatic cells transduced by retrovirus to express wild-type and ΔF508 CFTR. In these studies, cells were loaded with the halide-sensitive fluorophore, SPQ, and exposed to bath conditions that capitalize on the large difference in fluorescence quenching of SPQ by iodide vs. $NO_3$ to monitor the cell's halide permeability. Both I and $NO_3$ traverse the cAMP-activated Cl channel. It was found that SPQ fluorescence increases at a basal rate when I-loaded cells are exposed to $NO_3$. Subsequent addition of a cAMP cocktail (CT) produced a marked increase in the rate of fluorescence dequenching in cells transduced with wild-type CFTR, but had no effect in the ΔF508-expressing cells.

The assay is performed using fluorescence video microscopy so that the halide permeability of individual cells is assessed. This permits the percentage of cells in the entire cell population that respond to cAMP to be monitored. The percent of responding cells can be compared with transduction efficiency assays using reporter genes. In addition, this assay is applicable for assessing the effects of in vitro transduction and for primary airway cell cultures obtained from animals exposed to recombinant AAV viruses Immunofluorescence localization of CFTR has been performed on transduced cells using a commercially available monoclonal antibody (Genzyme MAb13-1). Preliminary studies have been performed in CFPAC cells transduced to express wild-type CFTR. The immunofluorescent staining pattern observed in a field of CFPAC-1 cells under basal conditions has already been established. Cytoplasmic immunofluorescence showed a punctuate perinuclear staining pattern characteristic of the labeling of ER and Golgi, and at this depth of field, staining was also apparent in the plasma membrane, as a ring of fluorescence at the cell border. This staining pattern is much less intense in a genetic control, the parental CFPAC-1 cell line, which expresses low levels of CFTR mRNA. Control experiments performed with a monoclonal anti-tubulin antibody on the same cells showed filamentous microtubule labeling, and this indicated that the pattern observed with the anti-CFTR antibody is not due to non-specific secondary antibody labeling.

2. Delivery of Chemical Markers into Animal Lungs

The present inventors and colleagues are developing a practical method for delivering therapeutic reagents, including AAV based transducing particles, to the lung. Techniques to introduce fluorescent lipids into rabbit lungs as markers to monitor the efficiency and the distribution of delivery under different conditions are being developed.

Currently, a mixture of surfactant and fluorescent lipid can be delivered into respiratory bronchioles—the primary target for CF treatment. An average of 50% of the labeled surfactant can be recovered from peripheral lung tissue. In these studies it has been found that entire epithelial surfaces of the respiratory bronchiole can be covered by fluorescent lipid and that some fluorescein can be seen inside the alveoli or alveolar ducts.

The procedure is outlined as following: The surfactant (EXOSURF, Burroughs Wellcome Co.) was mixed with 1-Palmitoyl-2-[12-{(7-nitro-2-1,3-benzoxadialzol-4-yl) amino} dodecanoyl] Phosphatidylcholine (NBD-PC) in sterile water, then reverse phase rotoevaporation was performed to conjugate surfactant with the fluorescent lipid and to reduce the volume.

New England white, male rabbits weighing 1.5–2 kg, were anesthetized with ketamine (10 mg/KG) and halothane (1.5% in 4 l/min 100% oxygen) and secured to an operating table. A 20 ga. catheter was placed in the trachea through the cricothyroid membrane. 5 ml/Kg body weight of fluorescently labeled surfactant was injected through the catheter under pulse pressure synchronized with inspiration while slowly rotating the rabbit along its craniocaudal axis. After instillation the rabbits recovered in 15 minutes and were returned to their cages. Four hours post-delivery the tracheal canal of each rabbit was closed and the lungs were collapsed under anesthesia. After removing the lungs from the chest they were filled immediately with 60 ml of OCT Compound and frozen. Sliced sections of 5 µm thick were mounted on a Nikon Diaphot TMD inverted microscope equipped for epifluorescence. Images were taken with a Photometrics CH250 coupled charge device video camera connected to a Macintosh IIci computer and digitized with a IPlab Spectrum image analyzing program (Signal Analeptics Co., Vienna, Va.). Different levels of fluorescence intensity were visualized by pseudocolouring technique.

3. In Vitro Transfer of Marker Genes Into Airway Epithelial Cells

Cell lines: It is contemplated that several airway cell lines will be employed to avoid biasing results because of the properties of a single cell line. Using the reporter constructs, the infectivity of AAV virions in both T antigen and papilloma virus transformed cells will be assessed. Contemplated cell lines are: 2CFSMEo-, 3ACFSMEo- and 6CFSMEo-. These lines express low levels of mutant CFTR and have been shown to be capable of functional complementation using transfection procedures. Cells which are post-crisis and are amenable only to functional assays that do not require resistive monolayers (e.g. anion efflux or SPQ). Cells which are pre-crisis (human papilloma virus transformed airway cells) form resistive monolayers that permit transepithelial measurements.

Primary cultures: To determine what cell types AAV will infect, primary airway cell cultures will be employed using β-gal as the maker gene. A limited number of studies will be performed to assess the tropism of AAV. For these studies, airway cells will be harvested from adult rabbits by collagenase and trypsin digestion. These cells will be cultured in several 35 mm plates and exposed to hybrid virions ($10^6$–$10^8$ particles per plate). 72 hr post-infection, cells will be fixed with 2% formaldehyde in PBS and stained with X-gal. The proportion and subtype of stained cells will be analyzed morphologically and scored using standard techniques.

4. Functional Expression of CFTR

From a functional viewpoint, the most commonly accepted, and the most intensively studied, cellular defect in CF epithelial cells lies in the regulation of Cl channels by cAMP-dependent protein kinase. The basis of this Cl conductance pathway, which contributes to fluid and electrolyte secretion in both airways and exocrine glands, is an 8–10 pS Cl channel with a linear current-voltage relation. The activity of these channels in normal, but not CF cells, has been discerned by a variety of assays, including isotopic flux, halide-sensitive fluorophores, transepithelial measurements and whole-cell and single-channel patch-clamp. These physiological assays are available for assessment of functional CFTR expression using the newly-designed AAV vectors of the present invention.

In vitro complementation assays will be performed initially by exposing human CF airway cell lines (see above) to AAV vectors carrying CFTR cDNA. CFTR expression will be assessed using functional and protein expression assays (see above). The time course and dose-response relations for functional expression of CFTR in CF airway cells will be determined. The video-based assay for SPQ fluorescence will permit the effects of time and virus dose on both the percent of cells responding and the rate of fluorescence increase (halide permeability) in responding cells to be determined. In other studies, the inventors have shown that the rate of fluorescence dequenching is proportional to the magnitude of Cl permeability increase elicited by cAMP.

The inventors will also demonstrate that the expressed conductance is that anticipated from CFTR using whole-cell patch-clamp. In cells ranging from insect to human, CFTR produces a cAMP-activated Cl-selective conductance pathway with specific biophysical properties. Several studies on airway cells will be performed to verify that this pathway arises from CFTR expression in the airway cell line chosen for these studies. Both the fluorescence and patch-clamp methods are well documented and known to those of skill in the art.

CFTR expression at protein level will be determined using indirect immunofluorescence in both functionally-responsive and non-responsive cell populations. Cells grown on collagen-coated glass coverslips (as for the functional studies) will be rinsed in PBS and fixed for immunofluorescence studies using absolute methanol fixation for 7 min at 20° C. followed by permeabilization with 0.5% Triton X-100 for 2 min. Cells will then be incubated in an appropriate dilution of antibody directed against CFTR (Genzyme MAb13-1) for 30 min at 37° C. and subsequently washed. Cells will then be incubated in secondary antibody (FITC-conjugated goat anti-mouse IgG; Boehringer Manneheim) for 30 min at 37° C. and rinsed. Finally, cells will be stained with Hoescht 33258 (Calbiochem) for nuclear visualization. The coverslips will then be mounted on slides in 1:9 PBS:glycerol containing 1% phenylene diamine. Negative controls will be performed by omitting the primary antibody or by using mouse IgG. Other negative controls will include untreated parental cells, which expresses very low CFTR mRNA levels. Slides will be examined using a Leitz Vario Orthomat 2 equipped for epifluorescence. The fluorescence intensities and percent of expressing cells will be quantitated using Image 1/FL software (Universal Imaging).

For determination of the relation between CFTR expression and transport responsiveness of the epithelial monolayers, the monolayer cultures will be examined en face to determine the percent of cells expressing CFTR protein by cell counting (relative to nuclei, identified with Hoescht stain). The data will be compared with the percent transport responsiveness of these preparations (from the SPQ assays, see below) to determine whether uniform CFTR expression is required for maximal responsiveness or whether a small percentage of cells expressing CFTR at high levels can rescue the complete functional responsiveness of the sepreparations. Recent studies suggest that as few as 10% of transfected cells can produce wild-type electrical responses in human airway cell monolayers.

The inventors will establish primary cultures of tracheal epithelial cells from adult rabbits. For the transepithelial measurements, these cells will be seeded on collagen films attached to polycarbonate rings. The electrical properties of the monolayer will be determined under current or voltage clamp. Chloride secretion under basal conditions will be determined from the change in short-circuit current (Isc) observed when $10^{-4}$ M bumetanide is added to the basolateral solution. Na absorption will be determined from the decrease in Isc in response to addition of $10^{-4}$ M amiloride to the luminal bath in the continued presence of bumetanide. Following removal of both drugs, Cl secretion will be stimulated by addition of isoproterenol (1 $\mu$M) to the basolateral solution and the additions of furosemide and amiloride will be repeated to determine the effects of the β-agonist on the Cl and Na currents. Then tissues will be fixed (using conditions cited above) and subjected to indirect immunofluorescence for correlation with CFTR expression.

5. Evaluation of the Efficacy of Gene Therapy in CF Mice

Successful genetic complementation of CF cells with a MLV derived retrovirus vector provided evidence that gene therapy for CF could succeed. The inventors propose that using AAV vectors to increase the specificity of infection and efficiency of integration into quiescent epithelial cells in the airway will lead to a practical protocol for transferring the CFTR gene into the airways of patients. Although it is promising that gene therapy can eventually provide a permanent cure for CF, there is no direct data to support the efficacy of gene therapy for CF in vivo. This is partly due to the lack of an efficient gene transfer approach.

CF mice, created by targeted interruption of the CFTR gene, develop serious intestinal obstructions similar to those in humans and the majority of them die within 6 weeks after birth. Although the harsh condition in the digestive system will prevent other means of gene delivery to test the efficacy of gene therapy, the CF mice do provide a valuable model for gene therapy of CF using DNA virus based vectors since these viruses are known to survive in the intestine. The basic mechanism for the pathological symptoms in the digestive system and lungs is likely to be the same, that is the thickened gland secretion blocked the gland duct cause the mucous to accumulate, solidify, fiborize and eventually block the airway or intestinal passage. Thus the efficacy of gene therapy for the digestive system is expected to reflect that in the respiratory system. The short pathological course of the CF mice also provide a convenient model to compare the pathological development with and without the CFTR gene transduction. This will provide direct evidence to support the efficacy of gene therapy for CF.

To evaluate the therapeutic effect of CFTR gene transfer, AAV particles containing the CFTR gene will be introduced into the intestine of CF mice using a silicon rubber catheter (0.5 mm of diameter) in a way analogous to that of a duodenal endoscope. An alternative approach is to directly insert the catheter into duodenum through an insection in the abdomen. Prior to the operation, the mice will be feed with 20% glucose solution only for 2 to 3 days to reduce the content of intestine. The digestive system will be prewashed with isotonic TBS to remove its contents and neutralize the pH with a catheter connected with a 1 CC syringe. $10^9$ transduce particles suspended into 0.5 ml of TBS will be injected into the intestine through the catheter. After 8 h incubation the mice will be feed with normal liquid diet.

The efficacy of this AAV mediated gene therapy will be analyzed physiologically and histopathologically. For physiological study, four days post transduction, CF mice will be scarified and the small intestine will be dissected, washed with isotonic PBS. The intestine membrane will be carefully removed and mounted in Ussing chambers. The cAMP-dependent Cl channel activity will be tested in a similar approach. The pathology in the intestine of the CF mice transduced with CF gene will be analyzed in comparison with that of untransduced CF mice. This group of mice will be kept until their natural death. The life span, general condition such as body weight, nutrition, and development will be evaluated in comparison with untreated CF mice. The intestine will be excised, stained and evaluated macroscopically for mucous obstruction, fibrosis as well as microscopically for histopathological analysis, such as scoring for mucus filled "bloom cells". Ideally, the transduced mice will have longer life spans and minor or no pathological changes in the intestine. Never the less, these experiments will provide valuable information regarding whether complementing of the CFTR defect in animal can prevent or reduce the pathological development of CF before an advanced pathological condition has developed. This kind information is unlikely to be obtained in the initial clinical trial, since only highly advanced patient are proposed to be tested due to ethical reasons.

6. Optimization for Efficient Transfer of CFTR Gene Into Lungs of Animal Models Gene delivery in vivo is complicated by the anatomy of the target tissue and host defense mechanisms. To test the efficiency and to optimize the protocols, the inventors will perform in vivo studies with reporter gene constructs to target the following goals:

(a) Methods of Gene transfer In Vivo

AAV virions survive most harsh physical treatments that retrovirus and adenovirus can not tolerate, for example heat inactivation and strong sonication. This makes it possible to deliver AAV to the airway using an ultrasonic nebulizer as well as spray inhalers (Metered Dose Inhaler). Virions collected from transfection medium can be directly pelleted with ultracentrifugation and further cleaned by pelleting the virus through 30% sucrose cushion or banded in CiCl gradients. This concentrated transducing viruses will be suspended in saline for aerosolization.

The aerosol will be delivered using a VISAN-9 nebulizer (Vortran Medical Technology, Sacramento, Calif.) adapted for small animals. For larger animals, e.g. rabbit, the aerosol will be delivered directly in the lung via an endotracheal tube while the animal is under anesthesia (2% halothane). Concentrated virus also will be delivered into the respiratory tract using a modified metered dose inhaler with spraying nozzle attached to the end of endotracheal tube. With this approach more concentrated virus can be delivered directly into deeper part of the lung and small airways. Delivery also can be done lobe-by-lobe with a pediatric fiberoptic bronchoscope. This will allow relatively large amounts of liquid to be delivered into the lobe to increase the efficiency of transduction. For small animals, like mice, a tiny mask connected to the nebulizer will be attached to the snout for aerosol delivery.

Initial studies will be performed using constructs containing the Lac-Z gene and CAT gene as a marker. The distribution of the transducing virion and number of transduced cells in the airway will be estimated by X-gal labeling of the chemically fixed airways. Viral dose and the form of the viral preparation will be optimized by examining the percentage of blue cells in transduced airways.

(b) The Stability of Transduced Genes in Animal Models

The duration of expression of integrated gene that are transduced with AAV vector will be studied using reporter genes in animal models. One major advantage of gene transfer with AAV vectors over adenovirus and transfection methods is that gene expression can be potentially permanent in the recipient cell due to the efficient integration of viral genome into host DNA. It is of interest to determine how long expression of the transferred gene will be sustained in vivo.

A group of 24 mice will be infected under optimized conditions with transducing virions containing the CAT gene (pMAVsvCAT vector). Four animals will be sacrificed at 1st, 2nd, 4th, 7th, 11th and 16th weeks. Airway epithelial cells of the sacrificed animals will be tested for the CAT activity. The CAT gene is used as the marker because the sensitivity of this assay. If a reasonable level of CAT gene activity can be detected at 16 weeks post transduction, longer period of time will be tested for gene expression. This study will allow the inventors to determine the persistence of expression of the transferred gene in vivo.

If there is a reduction in CAT gene expression, a similar study with lac Z gene as marker will be done to determine if the reduction is due to the reduced expression in transduced cells or the reduction of the number of the transduced population. In this study AAV virions containing lac-Z gene will be delivered into the airway of 28 mice and mice will be sacrificed at the same interval as the study using CAT gene. Bronchioles of these groups of mice will be dissected and stained with X-gal. The amount of blue cells will be estimated and compared under the microscope.

(c) In Vivo Studies of CFTR Gene Delivery

Although the CF mice do not exhibit any lung disease, their lack of CFTR expression in the airway provides an animal model for functional study of CFTR gene in transduced animals. After modifying the transport properties of intestine membrane of CF mice, the inventors propose to extend these studies to tracheal cells isolated from mice subjected to aerosolized AAV containing CFTR cDNA. Once isolated, the transepithelial properties would be quantified as described the in vitro studies and compared with those from empty vector controls. CFTR immunofluorescence would be used to assess the proportion of expressing cells for comparison with the reporter gene results and to determine the fraction and the type of transduced cells necessary to effect measurable changes in Cl secretion and/or Na absorption rates.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. All claimed matter and methods can be made and executed without undue experimentation.

REFERENCES

The following references, to the extent that they provide exemplary procedural or other details supplementary to those set forth herein, are specifically incorporated herein by reference.

Bauer and Monreal, 1988, Arch. Virol. 98:271.
Buller and Rose, 1978, J. Virol. 61:621.
Cukor et al., 1984, In: The Parvoviruses, Ed. K. I. Berns, Plenum, New York, pp. 33–66
Drumm et al., 1990, Cell 62:1227
Egan et al., 1992, Nature 358:581
Flotte et al., 1992, Cystic Fibrosis Conference, Washington, D.C.
Ghosh-Choudhury and Graham, 1987, Biochem. Biophys. Res. Comm. 147:964
Gluzman et al., 1982, in *Eukaryotic Viral Vectors* (Gluzman, Y., Ed.) pp. 187–192, Cold Spring Harbor Press, Cold Spring Harbor, N.Y.
Graham and Prevec, 1991, Methods in Molecular Biology. Clifton, N.J., The Humana Press Inc. 109–127.
Gregory et al., 1992, Cystic Fibrosis Conference, Washington, D.C.
Haj-Ahmad and Graham, 1986, L. Virol. 57:267–274.
Hidaka et al., 1989, Trans. Assoc. Am. Physicians 102:91–100.
Hogan et al., 1972, Amsterdam: Noth-Holland, p243
Keeler et al., 1986, Gene 50:215.
Kotin et al., 1990, Proc. Natl. Acad. Sci. USA 87:2211
Lebkowsi et al., U.S. Pat. No. 5,173,414, 1992
Lebkowski et al., 1988, Mol. Cell. Biol. 8 (10):3988
McGrory et al., 1988, Virol. 163:614
McPherson and Rosenthal, 1985, Virology 147:217.
Meignier et al., 1987, In "Vaccines 87: Modern approaches to new vaccines," Chanock, et al., Cold Spring Harbor Laboratory, Cold Spring Harbor, N.Y. 368.
Miller 1992, Curr. Top. Microbiol. Immunol. 158:1
Mocarski et al., 1980, Cell 22:243.
Mulligan, 1993, Science 260:926
Muzyczka, 1992, Curr. Top. Microbiol. Immunol. 158:97
Muzyczka et al., U.S. Pat. No. 5,139,941, 1992
Ostrove et al., 1981, Virology, 113:521
Page et al., 1993, Page, Keystone Symposium-Gene Therapy, Keystone, Colo., Wiley-Liss, Inc.
Parks et al., 1967, J. Virol. 1:171.
Post and Roizman, 1981, Cell 25:227.
Riordan et al., 1989, Science 245:1066; [published erratum appears in Science, 1989, 245:1437]
Rosenfeld et al., 1992, Cell 68:143
Sambrook et al. (1989). Molecular cloning: A laboratory manual. Cold Spring Harbor Laboratory. Cold Spring Harbor, N.Y.
Samulski et al., 1987, J. Virol. 61:3096
Samulski et al., 1989, J. Virol. 63:3822
Samulski et al., 1991, Embo J 10:3941
Shenk et al., 1980, Cold Spring Harbour Symp. Quant. Biol. 44:367
Shi et al., 1991, Cell 67:377
Spessor et al., 1989, Virology 168:378
Stewart et al., 1992, Hum. Gene Ther. 3:267
Torchilin et al., 1992, Faseb J. 6:2716
Walsh et al., 1992, Proc. Natl. Acad. Sci. USA 89 (15):7257
Zhu, et al., 1993, Science 261:209–211.

What is claimed is:

1. A herpes virus vector construct comprising a recombinant insert including an expression region comprising an essential adeno-associated virus (AAV) gene and sequences that enable packaging of said vector into infectious herpes virus virions, wherein said herpes virus vector is selected from the group consisting of herpes simplex virus (HSV), cytomegalovirus (CMV), pseudorabies virus (PRV) and Epstein-Barr Virus (EBV).

2. An adenovirus or herpes virus vector construct comprising a recombinant insert including an AAV vector comprising AAV ITR sequences and an expression region encoding a recombinant protein, the AAV vector being capable of integrating into a host cell genome.

3. An adenovirus vector in which the E1 and E3 or part or all of E4 region has been deleted and replaced by a recombinant adeno-associated virus (AAV) vector insert comprising AAV inverted terminal repeat (ITR) sequences and an expression region encoding a recombinant protein, wherein said AAV vector is capable of integrating into a host cell genome.

4. A recombinant adenovirus or herpes virus virion which contains a vector construct comprising a recombinant insert which includes an AAV vector comprising AAV ITR sequences and a transcription unit encoding a recombinant protein, the AAV vector being capable of integrating into a host cell genome and expressing a recombinant protein.

5. A recombinant host cell comprising (a) an AAV vector integrated into the genome of said cell, wherein said AAV vector comprises AAV ITR sequences and sequence encoding a transgene; and (b) an adenovirus or herpes virus vector encoding an essential AAV protein.

6. A method for producing recombinant AAV virions, comprising the steps of:
　(a) infecting a host cell with a first recombinant adenovirus or herpes virus that contains a recombinant AAV vector encoding a selected protein;
　(b) infecting said host cell with a second recombinant adenovirus or herpes virus that contains a vector encoding essential AAV proteins; and
　(c) culturing said infected cell to obtain the recombinant AAV virions.

7. The method of claim 6, wherein said second recombinant virus comprises a vector construct expressing the AAV rep and cap genes.

8. The method of claim 6, wherein said second recombinant virus is a replication-defective virus and the host cell complements the defect.

9. The method of claim 6, wherein said second recombinant virus is replication-defective and the host cell is infected with a third recombinant virus which complements the defect.

10. The method of claim 6, wherein the recombinant AAV vector is integrated into the genome of the host cell.

11. The method of claim 6, wherein the recombinant AAV vector includes AAV ITR sequences and an expression region including an exogenous gene.

12. The method of claim 11, wherein the AAV vector includes an expression region including a nucleic acid sequence encoding a full length CFTR protein.

13. A method for producing recombinant AAV virions, comprising obtaining recombinant AAV virions from a cultured host cell infected with:
　(a) a recombinant adenovirus containing a vector in which the E1 region has been replaced with an AAV vector construct comprising an expression region encoding a selected protein, the AAV vector being capable of integrating into the host cell genome;
　(b) a recombinant adenovirus containing a vector in which the E3 region has been replaced with the AAV rep-lip genes, the vector expressing the lip protein; and
　(c) a recombinant adenovirus containing a vector in which the E3 region has been replaced with the AAV cap gene, the vector expressing the cap protein.

* * * * *